US011248197B2

(12) United States Patent
Bootsma

(10) Patent No.: US 11,248,197 B2
(45) Date of Patent: *Feb. 15, 2022

(54) PROCESSES FOR RECOVERING PRODUCTS FROM A CORN FERMENTATION MASH

(71) Applicant: POET GRAIN (OCTANE), LLC, Sioux Falls, SD (US)

(72) Inventor: Jason Bootsma, Wichita, KS (US)

(73) Assignee: POET GRAIN (OCTANE), LLC, Sioux Falls, SD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/529,025

(22) PCT Filed: Nov. 23, 2016

(86) PCT No.: PCT/US2016/063666
§ 371 (c)(1),
(2) Date: May 23, 2017

(87) PCT Pub. No.: WO2017/091766
PCT Pub. Date: Jun. 1, 2017

(65) Prior Publication Data
US 2018/0044620 A1  Feb. 15, 2018

Related U.S. Application Data

(60) Provisional application No. 62/324,159, filed on Apr. 18, 2016, provisional application No. 62/260,181, filed on Nov. 25, 2015.

(51) Int. Cl.
C12P 7/02 (2006.01)
C12P 19/14 (2006.01)
C12N 1/20 (2006.01)
C12F 3/10 (2006.01)
C12F 3/02 (2006.01)
C12C 11/00 (2006.01)
B01D 3/00 (2006.01)
B01D 33/06 (2006.01)
B01D 39/08 (2006.01)
C07C 29/80 (2006.01)

(52) U.S. Cl.
CPC ............... C12F 3/10 (2013.01); B01D 3/002 (2013.01); B01D 33/06 (2013.01); B01D 39/083 (2013.01); C07C 29/80 (2013.01); C12C 11/00 (2013.01); C12F 3/02 (2013.01); Y02E 50/17 (2013.01)

(58) Field of Classification Search
CPC .............. C12P 19/14; C12P 7/14; C12P 19/02
USPC .................... 435/161, 162, 252.2
See application file for complete search history.

(56) References Cited

U.S. PATENT DOCUMENTS

| 2,446,913 | A | 8/1948 | Erlich |
| 2,478,937 | A | 8/1949 | Niethamer |
| 2,698,826 | A | 1/1955 | Peltzer |
| 3,538,551 | A | 11/1970 | Joa |
| 3,761,027 | A | 9/1973 | Mendoza |
| 4,056,636 | A | 11/1977 | Muller |
| 4,361,651 | A | 11/1982 | Keim |
| 4,565,330 | A | 1/1986 | Katoh |
| 5,195,684 | A | 3/1993 | Radzins |
| 5,250,182 | A | 10/1993 | Bento et al. |
| 5,662,810 | A | 9/1997 | Willgohs |
| 5,795,477 | A | 8/1998 | Herman et al. |
| 6,106,673 | A | 8/2000 | Walker |
| 6,117,321 | A | 9/2000 | Johnston |
| 6,230,995 | B1 | 5/2001 | Niemi et al. |
| 6,475,132 | B2 | 11/2002 | Zettier |
| 6,509,180 | B1 | 1/2003 | Verser et al. |
| 6,962,722 | B2 | 11/2005 | Dawley et al. |
| 7,083,954 | B2 | 8/2006 | Jakel et al. |
| 7,101,691 | B2 | 9/2006 | Kinley et al. |
| 7,300,680 | B2 | 11/2007 | Prevost et al. |
| 7,384,010 | B2 | 6/2008 | Horigane et al. |
| 7,497,955 | B2 | 3/2009 | Scheimann et al. |
| 7,507,562 | B2 | 3/2009 | Verser et al. |

(Continued)

FOREIGN PATENT DOCUMENTS

| AU | 2833395 A | 2/1996 |
| WO | 2005029974 A1 | 4/2005 |

(Continued)

OTHER PUBLICATIONS

Pleasant Hill Grain, website catalog pp. 1-8, ABC Hansen Disc Mill, Aug. 9, 2015.
Particle Size Distributions of Ground Corn and DDGS from Dry Grind Processing, Rausch et al., Transactions of the ASAE, Vol. 48(1), pp. 273-277, 2005.
Disc Mill DM 400-Retsch, Powerful grinding and robust design, Aug. 19, 2015.
Ethanol Producers Talk Shop, pp. 1-3, Ron Kotrba, Aug. 1, 2006.

(Continued)

Primary Examiner — Robert B Mondesi
Assistant Examiner — Mohammad Y Meah
(74) Attorney, Agent, or Firm — Kagan Binder, PLLC

(57) ABSTRACT

Processes and systems for recovering products from a corn fermentation mash. In one example, a process for recovering products from a corn fermentation mash can include separating ethanol from a fermentation mash to produce a whole stillage. The fermentation mash can be derived from a ground corn product milled from a plurality of corn pieces. The plurality of corn pieces can include whole corn kernels, fragmented corn kernels, size-reduced corn kernels, milled corn kernels, or a mixture thereof. Greater than 25 wt % of the ground corn product can have a particle size of greater than 105 μm and greater than 80 wt % of the ground corn product can have a particle size of 425 μm or less, as measured according to AOAC 965.22-1966. The process can also include separating the whole stillage to produce a fiber rich portion and a filtrate.

19 Claims, 7 Drawing Sheets

(56) References Cited

U.S. PATENT DOCUMENTS

| | | |
|---|---|---|
| 7,572,353 B1 | 8/2009 | Vander Griend |
| 7,601,858 B2 | 10/2009 | Cantrell et al. |
| 7,608,729 B2 | 10/2009 | Winsness et al. |
| 7,699,255 B2 | 4/2010 | Kapper |
| 7,829,680 B1 | 11/2010 | Sander et al. |
| 7,842,484 B2 | 11/2010 | Lewis |
| 7,857,608 B2 | 12/2010 | Fabbricante et al. |
| 7,858,140 B2 | 12/2010 | Paustian et al. |
| 7,886,996 B2 | 2/2011 | Horigane et al. |
| 7,888,082 B2 | 2/2011 | Verser et al. |
| 7,915,458 B2 | 3/2011 | Bruckmayer |
| 7,919,289 B2 | 4/2011 | Lewis |
| 7,935,370 B1 | 5/2011 | Prevost et al. |
| 7,954,734 B2 | 6/2011 | Hata |
| 8,017,365 B1 | 9/2011 | Rein et al. |
| 8,093,023 B1 | 1/2012 | Prevost et al. |
| 8,103,385 B2 | 1/2012 | Macharia et al. |
| 8,126,606 B2 | 2/2012 | Hung |
| 8,168,037 B2 | 5/2012 | Winsness |
| 8,192,627 B2 | 6/2012 | Gallop et al. |
| 8,236,086 B2 | 8/2012 | Janssen et al. |
| 8,236,977 B2 | 8/2012 | Woods et al. |
| 8,257,951 B2 | 9/2012 | Prevost et al. |
| 8,449,728 B2 | 5/2013 | Redford |
| 8,454,802 B2 | 6/2013 | Redford |
| 8,524,473 B2 | 9/2013 | Hammond et al. |
| 8,563,282 B2 | 10/2013 | Galvez, III et al. |
| 8,597,917 B2 | 12/2013 | Medoff et al. |
| 8,603,786 B2 | 12/2013 | Redford |
| 8,679,353 B2 | 3/2014 | Winsness |
| 8,702,819 B2 | 4/2014 | Bootsma |
| 8,722,372 B2 | 5/2014 | Kiuchi et al. |
| 8,722,911 B2 | 5/2014 | Bleyer et al. |
| 8,735,544 B1 | 5/2014 | Prevost et al. |
| 8,748,141 B2 | 6/2014 | Lewis et al. |
| 8,778,433 B2 | 7/2014 | Lee |
| 8,813,973 B2 | 8/2014 | Lee et al. |
| 8,927,239 B2 | 1/2015 | Allen et al. |
| 8,956,460 B2 | 2/2015 | Ahmed et al. |
| 8,962,059 B1 | 2/2015 | Froderman et al. |
| 8,986,551 B2 | 3/2015 | Kohl et al. |
| 9,012,191 B2 | 4/2015 | Lee |
| 9,012,668 B2 | 4/2015 | Winsness |
| 9,029,126 B2 | 5/2015 | Bleyer et al. |
| 9,040,270 B2 | 5/2015 | Prevost et al. |
| 9,061,987 B2 | 6/2015 | Bootsma |
| 9,108,140 B2 | 8/2015 | Winsness |
| 9,114,114 B2 | 8/2015 | Anderson et al. |
| 9,150,790 B2 | 10/2015 | Thorn et al. |
| 9,169,498 B2 | 10/2015 | Woods et al. |
| 9,212,334 B2 | 12/2015 | Cantrell et al. |
| 9,320,990 B2 | 4/2016 | Winsness |
| 9,328,311 B2 | 5/2016 | Jenkins et al. |
| 9,340,767 B2 | 5/2016 | Narendranath |
| 9,353,332 B2 | 5/2016 | Lewis et al. |
| 9,375,731 B2 | 6/2016 | Dieker et al. |
| 9,376,504 B2 | 6/2016 | Dieker et al. |
| 9,388,475 B2 | 7/2016 | Lee |
| 9,516,891 B1 | 12/2016 | Roa-Espinosa |
| 9,631,161 B2 | 4/2017 | Sungail et al. |
| 9,695,381 B2 | 7/2017 | Lee |
| 9,714,267 B2 | 7/2017 | Emanuele et al. |
| 9,718,006 B2 | 8/2017 | Lee |
| 9,730,463 B1 | 8/2017 | Roa-Espinosa |
| 9,745,540 B2 | 8/2017 | Sungail et al. |
| 9,896,643 B2 | 2/2018 | Redford |
| 10,059,966 B2 | 8/2018 | Bootsma |
| 10,093,891 B2 | 10/2018 | Kohl et al. |
| 10,113,007 B2 | 10/2018 | Kohl |
| 10,214,559 B2 | 2/2019 | Modinger et al. |
| 10,260,031 B2 | 4/2019 | Gallop et al. |
| 10,400,201 B2 | 9/2019 | Yu |
| 10,745,643 B2 | 8/2020 | Gallop et al. |
| 10,774,303 B2 | 9/2020 | Dieker et al. |
| 10,837,029 B2 | 11/2020 | Bootsma et al. |
| 11,078,500 B2 | 8/2021 | Hansen et al. |
| 2004/0087808 A1 | 5/2004 | Prevost et al. |
| 2004/0192896 A1 | 9/2004 | Finch |
| 2004/0234649 A1 | 11/2004 | Lewis et al. |
| 2005/0233030 A1 | 10/2005 | Lewis et al. |
| 2005/0239181 A1 | 10/2005 | Lewis et al. |
| 2006/0194296 A1 | 8/2006 | Hammond et al. |
| 2007/0031953 A1 | 2/2007 | Dunson, Jr. et al. |
| 2007/0036881 A1 | 2/2007 | Griffith |
| 2007/0141691 A1 | 6/2007 | Hirl |
| 2007/0148318 A1 | 6/2007 | Rubio et al. |
| 2007/0190626 A1 | 8/2007 | Wilkening et al. |
| 2007/0238691 A1 | 10/2007 | Thompson et al. |
| 2007/0254089 A1 | 11/2007 | Hickey et al. |
| 2008/0009048 A1 | 1/2008 | Bhargava et al. |
| 2008/0110577 A1 | 5/2008 | Winsness |
| 2008/0193991 A1 | 8/2008 | Allen et al. |
| 2008/0277264 A1 | 11/2008 | Sprague |
| 2009/0093027 A1 | 4/2009 | Balan et al. |
| 2009/0176289 A1 | 7/2009 | Friedmann |
| 2009/0250412 A1 | 10/2009 | Winsness et al. |
| 2009/0269817 A1 | 10/2009 | Lantero |
| 2009/0311397 A1 | 12/2009 | Whalen et al. |
| 2010/0055741 A1 | 3/2010 | Galvez, III et al. |
| 2010/0159519 A1 | 6/2010 | Diner et al. |
| 2010/0199062 A1 | 8/2010 | Sancho-Dominguez et al. |
| 2010/0221804 A1 | 9/2010 | Veit et al. |
| 2010/0281765 A1 | 11/2010 | Schwartz |
| 2011/0003341 A1 | 1/2011 | Nojiri et al. |
| 2011/0086149 A1 | 4/2011 | Bootsma |
| 2011/0142788 A1 | 6/2011 | Sellier et al. |
| 2011/0143411 A1 | 6/2011 | Yuan et al. |
| 2012/0051980 A1 | 3/2012 | Gallop et al. |
| 2012/0064213 A1 | 3/2012 | Lee |
| 2012/0244590 A1 | 9/2012 | Lee |
| 2013/0165678 A1 | 6/2013 | Kohl et al. |
| 2013/0295661 A1 | 11/2013 | Roesch et al. |
| 2014/0024084 A1 | 1/2014 | Galvez, III et al. |
| 2014/0110512 A1 | 4/2014 | Lee |
| 2014/0155639 A1 | 6/2014 | Sticklen et al. |
| 2014/0178946 A1 | 6/2014 | Galvez, III et al. |
| 2014/0242251 A1 | 8/2014 | Bootsma |
| 2014/0273166 A1 | 9/2014 | Narendranath |
| 2014/0315259 A1 | 10/2014 | Woods |
| 2015/0024451 A1 | 1/2015 | Williams |
| 2015/0037857 A1 | 2/2015 | Redford |
| 2015/0056327 A1 | 2/2015 | Redford |
| 2015/0076078 A1 | 3/2015 | Gallop |
| 2015/0118727 A1 | 4/2015 | Escudero et al. |
| 2015/0147786 A1 | 5/2015 | Clarkson et al. |
| 2015/0152196 A1 | 6/2015 | Phanopoulos et al. |
| 2015/0181911 A1 | 7/2015 | Redford |
| 2015/0181912 A1 | 7/2015 | Redford |
| 2015/0182882 A1 | 7/2015 | Gallop et al. |
| 2016/0024406 A1 | 1/2016 | Javers et al. |
| 2016/0145650 A1 | 5/2016 | Lewis et al. |
| 2016/0222135 A1 | 8/2016 | Lee |
| 2017/0051322 A1 | 2/2017 | Bushong et al. |
| 2017/0107452 A1 | 4/2017 | Dasari et al. |
| 2017/0114293 A1 | 4/2017 | Jakel et al. |
| 2017/0166834 A1 | 6/2017 | Jakel |
| 2017/0166835 A1 | 6/2017 | Jakel |
| 2017/0226165 A1 | 8/2017 | Franko et al. |
| 2017/0253892 A1 | 9/2017 | Bootsma |
| 2017/0268024 A1 | 9/2017 | Bootsma et al. |
| 2018/0016602 A1 | 1/2018 | Franko et al. |
| 2018/0044620 A1 | 2/2018 | Bootsma |
| 2018/0126302 A1 | 5/2018 | Gallop |
| 2018/0242626 A1 | 8/2018 | Froderman et al. |
| 2018/0355387 A1 | 12/2018 | Javers et al. |
| 2019/0017080 A1 | 1/2019 | Bootsma |
| 2020/0140899 A1 | 5/2020 | Bootsma |
| 2021/0017547 A1 | 1/2021 | Bootsma |
| 2021/0251256 A1 | 8/2021 | Gibbons et al. |

FOREIGN PATENT DOCUMENTS

| | | |
|---|---|---|
| WO | 2017059083 A1 | 4/2017 |
| WO | 2017/091766 A1 | 6/2017 |

(56) References Cited

FOREIGN PATENT DOCUMENTS

| WO | 2017091760 A1 | 6/2017 |
|---|---|---|
| WO | 2018215965 A1 | 11/2018 |
| WO | 2018217202 A1 | 11/2018 |

OTHER PUBLICATIONS

Fluid Quip-Ethanol Industry, Corn Wet Milling Process Description, website pp. 1-6, Aug. 19, 2015.
International Standard, ISO13320, Particle size analysis—Laser diffraction methods, pp. 1-58.
PCT/US2016/063657 International Search Report and Written Opinion, dated Feb. 7, 2017.
PCT/US2016/063666 International Search Report and Written Opinion, dated Mar. 27, 2017.
A Lecture on Pressure Screening, James A. Olson, Mechanical Engineering Department, University of British Columbia, Aug. 21, 2003.
Sluiter, A., et al., "Determination of Total Solids in Biomass and Total Dissolved Solids in Liquid Process Samples", National Renewable Energy Laboratory, pp. 1-9, 2008.
Sluiter, A., et al., "Determination of Ash in Biomass", National Renewable Energy Laboratory, pp. 1-8, 2005.
Hames, B., et al., "Determination of Protein Content in Biomass", National Renewable Energy Laboratory, pp. 1-8, 2008.
Sluiter, A., et al., "Determination of Extractives in Biomass", National Renewable Energy Laboratory, pp. 1-12, 2005.
Sluiter, A., et al., "Determination of Structural Carbohydrates and Lignin in Biomass", National Renewable Energy Laboratory, pp. 1-18, 2012.
Sluiter, A., et al., "Determination of starch in solid biomass samples", National Renewable Energy Laboratory, pp. 1-7, 2005. (Abstract).
Ankom, "Acid Detergent Fiber in Feeds—Filter Bag Technique (for A2000 and A2000I)", ADF method, pp. 1-2, 2017.
Cheetham, et al., "Variation in crystalline type with amylose content in maize starch granules: an X-ray powder diffraction study", Carbohydrate Polymers, vol. 36, pp. 277-284, 1998.
Nara, S., et al., "Studies on the Relationship Between Water-satured State and Crystallinity by the Diffraction Method for Moistened Potato Starch", starch, vol. 35, Issue 12, pp. 407-410, 1983. (Abstract).
Benedetti, A., et al., "X-ray diffraction methods to determine crystallinity and preferred orientation of lithium disilicate in Li—Zn-silicate glass-ceramic fibres", Journal of Materials Science, vol. 18, pp. 1039-1048, 1983. (Abstract).
Noureddini et al., "Stagewise Dilute-Acid Pretreatment and Enzyme Hydrolysis of Distillers' Grains and Corn Fiber", Appl Biochem Biotechnol, vol. 159, 2009, pp. 553-567.
Wongsagonsup et al., "Effects of different mill types on ethanol production using uncooked dry-grind fermentation and characteristics of residual starch in distiller's dried grains (DDG)", Cereal Chemistry, vol. 94, Feb. 27, 2017, pp. 645-653. (Abstract).
Chatzifragkou et al., "Biorefinery strategies for upgrading distillers' driedgrains with solubles (DDGS)", Process Biochemistry, vol. 50, 2015, pp. 2194-2207.
Kim et al., "Process simulation of modified dry grind ethanol plant with recycle of pretreated and enzymatically hydrolyzed distillers' grains", Bioresource Technology, vol. 99, 2008, pp. 5177-5192.
Rosentrater, "Production and use of evolving corn-based fuel ethanol coproducts in the U.S." In: Biernat (Editor): 11 Biofuels—Status and perspective, 2015, pp. 81-98.
PCT/IB2018/053688, International Search Report and Written Opinion, dated Aug. 21, 2018.
AOAC International "AOAC 965.22-1966", pp. 1, 1996.
Akinoso, R., et al. "Work Index and Milling Efficiency of Size Reduction of Maize Using Plate Mill", Agricultural Engineering today, vol. 36, pp. 22-28, 2012. (Abstract).
International Search Report and Written Opinion received for PCT application No. PCT/US2017/034324, dated Aug. 14, 2017, 8 pages.
International Preliminary Report on Patentability Chapter I of the PCT dated Dec. 5, 2019 in PCT/IB2018/053688.
International Preliminary Report on Patentability Chapter I of the PCT dated Dec. 5, 2019 in PCT/US2017/034324.
International Preliminary Report on Patentability Chapter I of the PCT dated Jun. 7, 2018 in PCT/US2016/063657.
International Preliminary Report on Patentability Chapter I dated Jun. 7, 2018 in PCT/US2016/063666.
Thin Stillage Solids Separation System, retrieved on Jun. 26, 2018 via http://www.icminc.com/products/lhin-stillagesolidsseparation-system.html, (2 pages).
About Harvesting Technology: Bringing Profitable Innovation for Ethanol Production, retrieved on Jun. 26, 2018 via http:/harvestingtech.com/#benefils, (11 pages).
Hunt, et al. "Corn Stillage as a Feedstuff for Broilers and Turkeys", Applied Poultry Science, Inc., Research Report 1997, published online at http://japr.fass.org/contenl/6/3/310.full.pdf, (9 pages).
Abdel-Tawwab et al., "Evaluation of commercial live bakers' yeast, Saccharomyces cerevisiae as a growth and immunity promoter for Fry Nile tilapia, Oreochromis niloticus (L.) challenged in situ with Aeromonas hydrophila", Aquaculture, vol. 280, Issues 1-4, pp. 185-189, 2008, (5 pages).
Kim et al., "Composition of corn dry-grind ethanol by-products: DOGS, wet cake, and thin stillage", Science Direct, Bioresource Technology, vol. 99, pp. 5165-5176, 2008, (12 pages).
Rausch et al.,"The Future of Coproducts From Corn Processing", Applied Biochemistry and Biotechnology, vol. 128, pp. 47-86, 2006, (40 pages).
Yamada et al., "Yeast (*Saccharomyces cerevisiae*) Protein Concentrate: Preparation, Chemical Composition, and Nutritional and Functional Properties", Journal of Agricultural and Food Chemistry, vol. 53, No. 10, pp. 3931-3936, 2005, (6 pages).

PROCESSES FOR RECOVERING PRODUCTS FROM A CORN FERMENTATION MASH

CROSS-REFERENCE TO RELATED APPLICATIONS

This is a National Stage Application under 35 U.S.C. § 371 of PCT/US2016/063666, filed on Nov. 23, 2016, which claims priority to U.S. Provisional Patent Application No. 62/324,159, filed on Apr. 18, 2016, and to U.S. Provisional Patent Application No. 62/260,181, filed on Nov. 25, 2015, which are all incorporated by reference herein.

BACKGROUND

Field

Embodiments described generally relate to processes and systems for recovering products derived from ground corn. More particularly, such embodiments relate to processes and systems for recovering products from a corn fermentation mash.

Description of the Related Art

Corn or maize is often used as a starch source to produce ethanol by fermentation. Corn is traditionally ground by a hammer mill in ethanol production facilities. Hammer milled corn has a very wide range of sizes and generally includes relatively large particle sizes.

The fermentation process produces a corn fermentation mash that includes a mixture of ethanol and multiple corn products. Ethanol is removed from the corn fermentation mash by distillation to produce a whole stillage that contains a mixture of corn products. Many of these corn products are too time consuming and/or costly to separate from the stillage and therefore are never recovered as separate products.

There is a need, therefore, for improved processes and systems for recovering products from a corn fermentation mash.

SUMMARY

Processes and systems for recovering products from a corn fermentation mash are provided. In one example, a process for recovering products from a corn fermentation mash can include separating ethanol from a fermentation mash to produce a whole stillage. The fermentation mash can be derived from a ground corn product milled from a plurality of corn pieces. The plurality of corn pieces can include whole corn kernels, fragmented corn kernels, size-reduced corn kernels, milled corn kernels, or a mixture thereof. Greater than 25 wt % of the ground corn product can have a particle size of greater than 105 µm and greater than 80 wt % of the ground corn product can have a particle size of 425 µm or less, as measured according to AOAC 965.22-1966. The process can also include separating the whole stillage to produce a fiber rich portion and a filtrate.

In another example, a process for recovering products from a corn fermentation mash can include separating ethanol from a fermentation mash to produce a whole stillage. The fermentation mash can be derived from a ground corn product milled from a plurality of corn pieces. The plurality of corn pieces can include whole corn kernels, fragmented corn kernels, size-reduced corn kernels, milled corn kernels, or any mixture thereof. The process can also include separating the whole stillage with one or more fiber filters to produce a fiber rich portion and a filtrate.

In another example, a process for recovering products from a corn fermentation mash can include separating ethanol from a fermentation mash to produce a whole stillage. The fermentation mash can be derived from a ground corn product milled from a plurality of corn pieces. The plurality of corn pieces can include whole corn kernels, fragmented corn kernels, size-reduced corn kernels, milled corn kernels, or any mixture thereof. The process can also include separating the whole stillage with a separator to produce a fiber rich portion and a filtrate. The separator can be or include a rotary drum screen, a rotary vacuum drum filter, a brush strainer, a vibratory separator, a linear motion screen, a vacu-deck screen, or a combination thereof.

BRIEF DESCRIPTION OF THE DRAWINGS

So that the manner in which the above recited features can be understood in detail, a more particular description, briefly summarized above, may be had by reference to embodiments, some of which are illustrated in the appended drawing. It is to be noted, however, that the appended drawing illustrate only typical embodiments and are therefore not to be considered limiting of its scope, for the invention may admit to other equally effective embodiments.

DETAILED DESCRIPTION

Figure 1:
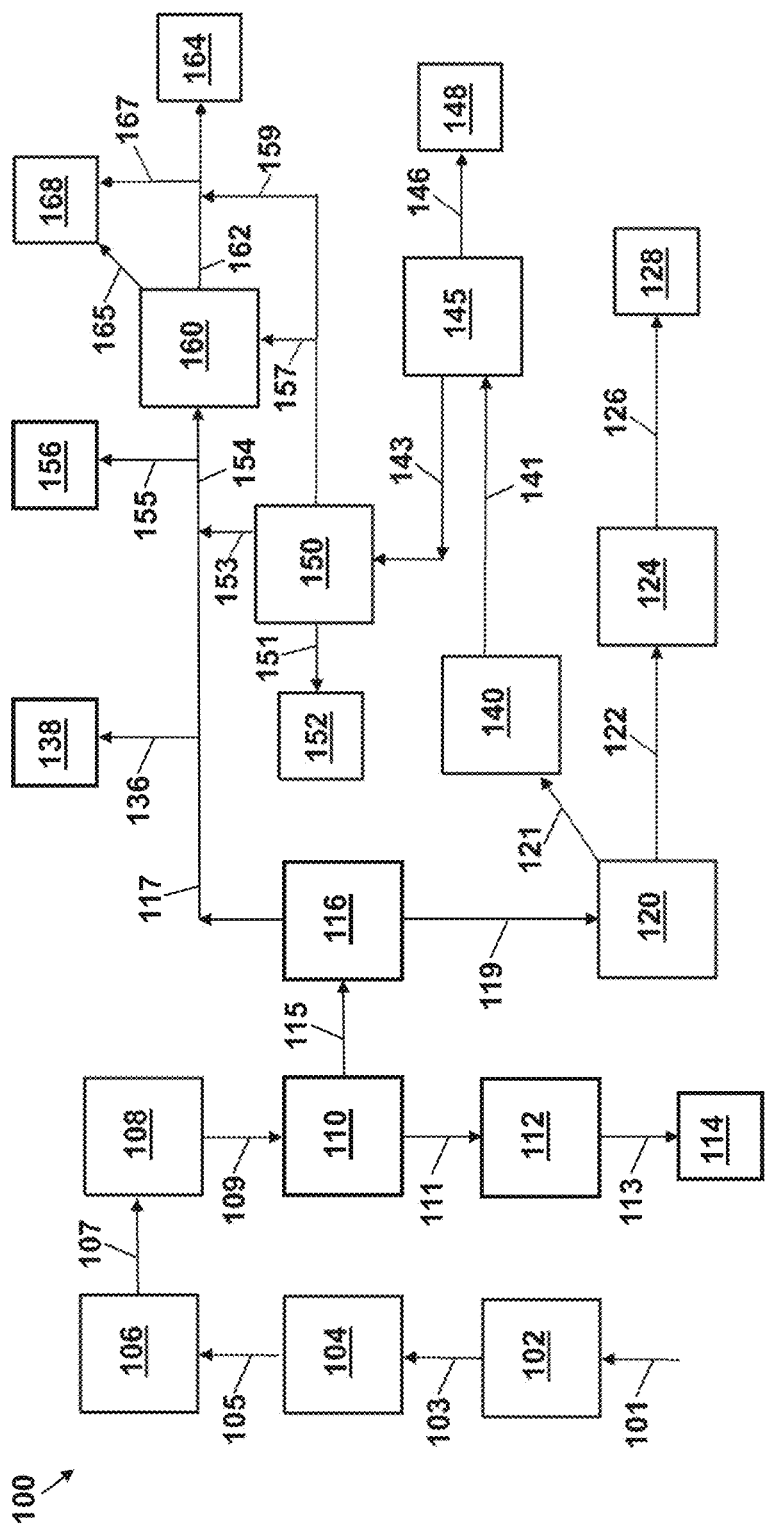
FIG. 1 depicts a schematic view of an illustrative system for recovering products derived from corn fermentation mash, according to one or more embodiments described.

FIG. 1 depicts a schematic view of an illustrative separation system 100 for recovering products derived from fermented corn. Illustrative products derived from fermented corn can include, but are not limited to, ethanol, distillers grains, protein rich products, oil, and other products. A ground corn product that can be produced from the corn, can be processed to produce the fermented corn. The ground corn product can be milled from a plurality of corn pieces by one or more high shear mills. For example, the plurality of corn pieces via line 101 can be introduced into one or more high shear mills 102. The corn pieces, prior to being high shear milled, can be or include, but are not limited to, whole corn kernels, fragmented corn kernels, size-reduced corn kernels, milled corn kernels, ground corn kernels, fresh corn kernels, dried corn kernels, or any mixture thereof. In some examples, whole corn kernels can be size-reduced via one or more non-high shear mills, such as one or more hammer mills and/or one or more roller mills using a non-shearing technique, to produce a coarse ground corn. The coarse ground corn can be further size-reduced, such as sheared, milled, or otherwise ground, in the high shear mill 102 to produce the ground corn product. The high shear mill 102 can be or include, but is not limited to, one or more disk mill fiberizers, one or more air swept pulverizers, one or more other high shear mills, or any combination thereof.

The ground corn product can have a particle size of less than a particle size of conventional ground corn (e.g., hammer milled corn or roller milled corn). For example, the ground corn product can have a $d_{50}$ by volume percent of about 100 μm to about 500 μm, as measured according to ISO 13320:2009. In contrast, hammer milled corn generally has a $d_{50}$ by volume percent of greater than 500 μm and roller milled corn generally has a $d_{50}$ by volume percent of greater than 600 μm.

In some examples, greater than 25 wt % of the ground corn product can have a particle size of greater than 105 μm and greater than 80 wt % of the ground corn product can have a particle size of 425 μm or less, as measured according to AOAC 965.22-1966. The particle size distribution of the ground corn product produced in the high shear mill is further discussed and described below. It has been surprisingly and unexpectedly discovered that when 80 wt % or more of the ground corn product has a particle size of 425 μm or less and when greater than 25 wt % of the ground corn product has a particle size of greater than 105 μm, one or more product yields (e.g., corn oil) and/or one or more system efficiencies is realized as compared to conventional ethanol production processes that use a ground corn in which less than 80 wt % of the ground corn has a particle size of 425 μm or less or when less than 25 wt % (e.g., less than 20 wt %) of the ground corn product has a particle size of greater than 105 μm.

The ground corn product produced in the high shear mill 102 can be processed or otherwise treated in one or more process units to produce a fermentation mash. The process units can include one or multiple vessels and/or apparatuses, such as slurry tanks and/or liquefaction tanks, for heating, mixing, separating, and/or carrying out other operations on the slurry. In some examples, the ground corn product via line 103 can be transferred from the high shear mill 102 to one or more slurry tanks 104. Other components or products from downstream in the separation system 100 can also be mixed, blended, or otherwise combined with the ground corn product in the slurry tank 104. The ground corn product can be mixed, blended, or otherwise combined with water and one or more enzymes, such as alpha-amylase, to produce a slurry tank mixture. One or more optional additives and/or one or more optional recycled downstream components can also be mixed, blended, or otherwise combined with the ground corn product, water, and enzyme to produce the slurry tank mixture. The slurry tank mixture can be processed to produce the fermentation mash. The slurry tank mixture can be heated to produce a gelatinized starch. The gelatinized starch can be hydrolyzed to produce a liquefaction mash. The liquefaction mash can be subjected to saccharification and fermentation to produce the fermentation mash.

The slurry tank mixture can be heated in a cooker (e.g., a pressurized jet cooker) to solubilize the starch in the ground corn product to produce a solubilized mixture of gelatinized starch. The slurry tank mixture can be mixed using a paddle mixer, a ribbon blender, a dense phase slurry mixer, or any combination thereof. The slurry tank mixture can be heated to a temperature that is at or above the onset of starch gelatinization where the alpha amylase can solubilize the starch. In one example, this temperature can be above the temperature where the onset of gelatinization occurs, but below the temperature needed to complete gelatinization. The starch is hydrolyzed by the enzyme into maltodextrins and oligosaccharides. Given sufficiently small particle size the hydrolysis can occur without complete gelatinization. Lower temperature liquefaction offers the benefit of reduced energy use and reduced damage to starch due to undesirable side reactions, such as the Maillard reaction, as well as a reduced formation of "dough balls", which are lumps of corn flour that can form in the slurry tank mixture and can reduce or cease the production of ethanol.

The slurry tank mixture in the slurry tank 104 can be heated to a temperature of less than 90° C., less than 85° C., less than 80° C., less than 75° C., less than 72° C., or less than 70° C. For example, the slurry tank mixture can be heated to a temperature of greater than 50° C., greater than 55° C., greater than 60° C., greater than 62° C., greater than 64° C., or greater than 66° C. to less than 90° C., less than 85° C., less than 80° C., less than 75° C., less than 72° C., or less than 70° C.

The solubilized mixture of gelatinized starch via line 105 can be transferred from the slurry tank 104 to one or more liquefaction tanks 106. One or more enzymes, such as alpha-amylase, can be added to the solubilized mixture of gelatinized starch in a liquefaction process to produce a liquefaction mash containing a hydrolyzed mixture. The enzyme can hydrolyze the gelatinized starch into maltodextrins and oligosaccharides.

The liquefaction mash via line 107 can be transferred from the liquefaction tank 106 to one or more fermenters 108. The liquefaction mash containing the hydrolyzed mixture can be further processed in one or more saccharification and fermentation processes to produce the fermentation mash. The saccharification and fermentation can occur sequentially or simultaneously. During saccharification, the liquefied mash can be cooled and one or more enzymes, such as glucoamylase, can be added to hydrolyze the maltodextrins and oligosaccharides into single glucose sugar molecules. During fermentation, one or more strains of yeast, such as *Saccharomyces cerevisae*, can be added to metabolize the glucose sugars into ethanol and carbon dioxide. After saccharification and fermentation, in some examples, the fermentation mash can include about 15 vol % to about 25 vol % of ethanol (volume/volume basis), as well as remaining grain components.

The fermentation mash via line 109 can be pumped or otherwise transferred from the fermenter 108 to one or more distillers 110 where the fermentation mash can be heated to vaporize at least a portion of the ethanol. The distiller 110 can be or include, but is not limited to, one or more distillation columns, one or more distillation trains, one or more condensers, or other device(s) configured to vaporize the ethanol and to condense the vaporized ethanol. The ethanol can be distilled or otherwise separated from the fermentation mash within the distiller 110 to produce a whole stillage. The whole stillage can include, but is not limited to, water, fibers, starches, oils, and proteins.

The vaporized ethanol can be condensed in a condenser within the distiller 110, and liquid alcohol (e.g., ethanol) can be recovered from the distiller 110 at about 95 vol % purity (190 proof). The 190 proof ethanol via line 111 can be transferred into one or more dehydrators 112 and dried. The dehydrator 112 can be or include one or more dehydration columns, such as molecular sieve dehydration columns. The 190 proof ethanol can pass through the dehydration columns in the dehydrator 112 that can remove residual water from the ethanol, to yield a drier product of purified ethanol, such as about 99.75 vol % of ethanol (about 199.5 proof) that can be transferred via line 113 to one or more ethanol storage containers 114.

The whole stillage left in the distiller 110 can be further processed to separate and/or recover a variety of products. Illustrative products that can be derived from the whole stillage can include, but are not limited to, other alcohols, oil products (e.g., a corn oil product), distillers grains (e.g., a wet fiber rich product, a wet fiber rich product with syrup, a dried fiber rich product, and/or a dried fiber rich product with syrup), protein products (e.g., a protein rich product), and/or other products from the whole stillage (e.g., a syrup product).

The whole stillage left in the distiller 110 can be transferred via line 115 to one or more separators 116. The whole stillage can be contacted or otherwise processed in the separator 116 to separate or otherwise produce a fiber rich portion via line 117 and a filtrate via line 119. For example, the fiber rich portion can be filtered or otherwise removed from stillage by the separator 116 to produce the filtrate that passes through the separator 116. The fiber rich portion can include fibrous material, such as fibers. The fiber rich portion can be used alone or combined with other components to produce various types of products, as will be further discussed and described below.

The separator 116 can be or include, but is not limited to, one or more pressure screens, one or more centrifuges (e.g., a filtration centrifuge such as those discussed and described in U.S. Pat. Nos. 8,813,973 and 8,778,433), one or more paddle screens, one or more fiber filters, one or more rotary drum screens, one or more rotary vacuum drum filters, one or more brush strainers, one or more vibratory separators, one or more centrifugal screeners, one or more linear motion screens, one or more vacu-deck screens, or any combination thereof.

In some examples, the separator 116 can be or include a single pressure screen. In other examples, the separator 116 can be or include two or more pressure screens. In other examples, the separator 116 can be a single pressure screen or two or more pressure screens and can be free of or otherwise exclude any centrifuge. In another example, the separator 116 be a single pressure screen or two or more pressure screens and can be free of or otherwise exclude any centrifuge, paddle screen, fiber filter, or any combination of centrifuge, paddle screen, and filter. In another example, the separator 116 can be a single pressure screen or two or more pressure screens and can be free of or otherwise exclude any centrifuge, paddle screen, fiber filter, rotary drum screen, rotary vacuum drum filter, brush strainer, vibratory separator, centrifugal screener, linear motion screen, and vacuum deck screen. As such, in at least one example, the whole stillage in line 115 can be separated into the fiber rich portion via line 117 and the filtrate via line 119 with only one or two or more pressure screens.

Illustrative pressure screens can be or include outflow pressure screens, inflow pressure screens, inflow/outflow pressure screens, and/or foils on accept side of plate pressure screens. In an outflow pressure screen, the whole stillage can flow from the inside of the screen plate cylinder to the outside, with the rotor being on the inside of the screen plate. The fibers can be held inside the plate until the fibers reach the reject port. In an inflow pressure screen, the whole stillage can flow from the outside of the screen cylinder to the inside with the rotor being on the outside of the screen plate. The fibers can be held on the outside of the cylinder. Suitable rotors can include foiled rotors, bump rotors, lobe rotors, and/or S-rotors. The openings in the pressure screens can be circular, slotted, or a combination thereof. The pressure screen can be made by milling slots into a single piece of metal and rolling the milled metal into a cylinder. The pressure screen can also be made by banding wires together to form a cylinder, which is also referred to as wedge-wire baskets.

Pressure screens that include slotted openings can have a width of about 12 µm, about 25 µm, about 50 µm, or about 75 µm to about 100 µm, about 130 µm, about 150 µm, about 175 µm, about 230 µm, about 255 µm, about 330 µm, about 380 µm, about 430 µm, about 500 µm, or more. In some examples, the pressure screen can include slotted openings having a width of about 10 µm, about 30 µm, about 50 µm, about 75 µm, about 100 µm, about 125 µm, or about 150 µm to less than 250 µm, less than 300 µm, less than 350 µm, less than 400 µm, less than 450 µm, or less than 500 µm.

In other examples, the separator 116 can be or include one or more fiber filters. In some examples, the separator 116 can be a single fiber filter. In other examples, the separator 116 can be a single fiber filter or two or more fiber filters. In other examples, the separator 116 can be a single fiber filter or two or more fiber filters and can be free of or otherwise exclude any centrifuge, any pressure screen, any paddle screen, or any combination of a centrifuge, pressure screen, and paddle screen. In another example, the separator 116 can be a single fiber filter or two or more fiber filters and can be free of or otherwise exclude any pressure screen, centrifuge, paddle screen, rotary drum screen, rotary vacuum drum filter, brush strainer, vibratory separator, centrifugal screener, linear motion screen, and vacuum deck screen. As such, in at least one example, the whole stillage in line 115 can be separated into the fiber rich portion via line 117 and the filtrate via line 119 with only one or two or more fiber filters.

The whole stillage can be introduced, e.g., pumped, into a filter sleeve of the fiber filter. The filter sleeve can have hole sizes or openings of about 12.7 µm, about 25.4 µm, about 50.8 µm, or about 76.2 µm to about 101.6 µm, about 127 µm, about 152.4 µm, about 177.8 µm, about 230 µm, about 255 µm, about 330 µm, about 380 µm, about 430 µm, about 500 µm, or more. In another example, the filter sleeve can have hole sizes or openings of about 10 µm, about 12 µm, about 25 µm, about 50 µm, or about 75 µm to about 100 µm, about 130 µm, about 150 µm, about 175 µm, about 230 µm, about 255 µm, about 330 µm, about 380 µm, about 430 µm, about 500 µm, or more. In some examples, the filter sleeve can have hole sizes or openings of about 10 µm, about 30 µm, about 50 µm, about 75 µm, about 100 µm, about 125 µm, or about 150 µm to less than 250 µm, less than 300 µm, less than 350 µm, less than 400 µm, less than 450 µm, or less than 500 µm.

The filter sleeve can be vibrated, e.g., at high frequency. For example, vibration of the filter sleeve can be accomplished by (1) tensioning the filter sleeve with a pair of springs, (2) rotating a high speed rotor disposed inside the filter sleeve that can induce pulsed waves in the whole stillage, or (3) a combination thereof. The rotor can include one or more flights that can push or otherwise urge solids toward a sludge discharge at the end of the fiber filter. For example, the rotor can include straight paddles with ribbon flighting that can direct solids toward the discharge. The pulsing and/or vibrations can also force or otherwise urge the filtered liquid through the filter sleeve. The filter sleeve can be made of one or more polymer fabrics. The polymer can be or include, but is not limited to, polyester, polyether ether ketone (PEEK), or other suitable polymers. The polymer fabric can be a woven polymer fabric. Any type of weave can be used to produce a filter sleeve composed of a woven polymer fabric. Illustrative types of weaves can include plain weave, twill weave, satin weave, basket weave, leno weave, and mock leno weave. The filter sleeve can be formed by connecting opposing edges of a filter sleeve by a lap or double hook joint. One suitable fiber filter can include the fiber filter discussed and described in U.S. Pat. No. 6,117,321. Some commercially available fiber filters can include, but are not limited to, the FF 6, the FF 12, and the FF 30, available from Vincent Corporation.

In other examples, the separator 116 can be or include one or more paddle screens. In some examples, the separator 116 can be a single paddle screen. In other examples, the separator 116 can be a single paddle screen or two or more paddle screens. In other examples, the separator 116 can be a single paddle screen or two or more paddle screens and can be free of or otherwise exclude any centrifuge, any pressure screen, and fiber filter, or any combination of a centrifuge, pressure screen, and fiber filter. In another example, the separator 116 can be a single paddle screen or two or more paddle screens and can be free of or otherwise exclude any pressure screen, centrifuge, fiber filter, rotary drum screen, rotary vacuum drum filter, brush strainer, vibratory separator, centrifugal screener, linear motion screen, and vacuum deck screen. As such, in at least one example, the whole stillage in line 115 can be separated into the fiber rich portion via line 117 and the filtrate via line 119 with only one or two or more paddle screens.

The paddle screen can include a screen that can include openings of about 12.7 µm, about 25.4 µm, about 50.8 µm, or about 76.2 µm to about 101.6 µm, about 127 µm, about 152.4 µm, about 177.8 µm, about 230 µm, about 255 µm, about 330 µm, about 380 µm, about 430 µm, about 500 µm, or more. In another example, the screen can have openings of about 12 µm, about 25 µm, about 50 µm, or about 75 µm to about 100 µm, about 130 µm, about 150 µm, about 175 µm, about 230 µm, about 255 µm, about 330 µm, about 380 µm, about 430 µm, about 500 µm, or more. In some examples, the screen can have openings of about 10 µm, about 30 µm, about 50 µm, about 75 µm, about 100 µm, about 125 µm, or about 150 µm to less than 250 µm, less than 300 µm, less than 350 µm, less than 400 µm, less than 450 µm, or less than 500 µm. A commercially available paddle screen can include, but is not limited to, the FQ-PS32 Paddle Screen available from Fluid-Quip, Inc.

In other examples, the separator 116 can be or include one or more rotary drum screens. In some examples, the separator 116 can be or include a single rotary drum screen. In other examples, the separator 116 can be or include a single rotary drum screen or two or more rotary drum screens. In other examples, the separator 116 can be or include a single rotary drum screen or two or more rotary drum screens and can be free of or otherwise exclude any pressure screen, centrifuge, paddle screen, fiber filter, rotary vacuum drum filter, brush strainer, vibratory separator, centrifugal screener, linear motion screen, and vacuum deck screen. As such, in at least one example, the whole stillage in line 115 can be separated into the fiber rich portion via line 117 and the filtrate via line 119 with only one or two or more rotary drum screens.

The rotary drum screen can include a filter element or screen having openings of about 10 µm, about 25 µm, about 50 µm, or about 75 µm to about 100 µm, about 130 µm, about 150 µm, about 175 µm, about 230 µm, about 255 µm, about 330 µm, about 380 µm, about 430 µm, about 500 µm, about 700 µm, about 900 µm, about 1 mm, about 1.5 mm, about 2 mm, or more. In some examples, the rotary drum screen can include openings of about 10 µm, about 30 µm, about 50 µm, about 75 µm, about 100 µm, about 125 µm, or about 150 µm to less than 250 µm, less than 300 µm, less than 350 µm, less than 400 µm, less than 450 µm, or less than 500 µm. A commercially available rotary drum screen can include, but is not limited to, the LIQUI-FUGE® LFS rotary drum screen available from Vulcan.

In other examples, the separator 116 can be or include one or more brush strainers. In some examples, the separator 116 can be or include a single brush strainer. In other examples, the separator 116 can be or include a single brush strainer or two or more brush strainers. In other examples, the separator 116 can be or include a single brush strainer or two or more brush strainers and can be free of or otherwise exclude any pressure screen, centrifuge, paddle screen, fiber filter, rotary drum screen, rotary vacuum drum filter, vibratory separator, centrifugal screener, linear motion screen, and vacuum deck screen. As such, in at least one example, the whole stillage in line 115 can be separated into the fiber rich portion via line 117 and the filtrate via line 119 with only one or two or more brush strainers. The brush strainer can include a casing surrounding a filter element or perforated strainer cylinder, through which the liquid can flow through. Particles suspended in the whole stillage can be held back in the cylinder and forced downward by rotating brushes mounted on a shaft.

The filter element or perforated strainer cylinder can have openings of about 10 µm, about 25 µm, about 50 µm, or about 75 µm to about 100 µm, about 130 µm, about 150 µm, about 175 µm, about 230 µm, about 255 µm, about 330 µm, about 380 µm, about 430 µm, about 500 µm, about 700 µm, about 900 µm, about 1 mm, about 1.5 mm, about 2 mm, or more. In some examples, the perforated strainer cylinder can include openings of about 10 µm, about 30 µm, about 50 µm, about 75 µm, about 100 µm, about 125 µm, or about 150 µm to less than 250 µm, less than 300 µm, less than 350 µm, less than 400 µm, less than 450 µm, or less than 500 µm. A commercially available brush strainer can include, but is not limited to, the W-SIL self-cleaning brush strainer, available from Alfa Laval.

In other examples, the separator 116 can be or include one or more rotary vacuum drum filters. In some examples, the separator 116 can be or include a single rotary vacuum drum filter. In other examples, the separator 116 can be or include a single rotary vacuum drum filter or two or more rotary vacuum drum filters. In other examples, the separator 116 can be or include a single rotary vacuum drum filter or two or more rotary vacuum drum filters and can be free of or otherwise exclude any pressure screen, centrifuge, paddle screen, fiber filter, rotary drum screen, brush strainer, vibratory separator, centrifugal screener, linear motion screen, and vacuum deck screen. As such, in at least one example, the whole stillage in line 115 can be separated into the fiber rich portion via line 117 and the filtrate via line 119 with only one or two or more rotary vacuum drum filters.

The rotary vacuum drum filter can include a vacuum pump, a filtrate pump, and a vacuum/filtrate receiver. The rotary vacuum drum filter can also include feed and/or drain pumps and pre-coat or chemical prep tanks. The drum can rotate while partially submerged in the whole stillage. A vacuum can draw liquid through the filter element or screen, e.g., a cloth or fabric filter element on the drum surface which retains the solids. The vacuum can pull a gas, e.g., air, through the cake and remove moisture as the drum rotates. The filter element can have openings of about 10 μm, about 25 μm, about 50 μm, or about 75 μm to about 100 μm, about 130 μm, about 150 μm, about 175 μm, about 230 μm, about 255 μm, about 330 μm, about 380 μm, about 430 μm, about 500 μm, about 700 μm, about 900 μm, about 1 mm, about 1.5 mm, about 2 mm, or more. In some examples, the filter medium can include openings of about 10 μm, about 30 μm, about 50 μm, about 75 μm, about 100 μm, about 125 μm, or about 150 μm to less than 250 μm, less than 300 μm, less than 350 μm, less than 400 μm, less than 450 μm, or less than 500 μm. A commercially available rotary vacuum drum filter can include, but is not limited to, the vacuum drum rotary filters available from Komline-Sanderson.

In other examples, the separator 116 can be or include one or more vibratory separators. In some examples, the separator 116 can be or include a single vibratory separator. In other examples, the separator 116 can be or include a single vibratory separator or two or more vibratory separators. In other examples, the separator 116 can be or include a single vibratory separator or two or more vibratory separators and can be free of or otherwise exclude any pressure screen, centrifuge, paddle screen, fiber filter, rotary drum screen, brush strainer, rotary vacuum drum filter, centrifugal screener, linear motion screen, and vacuum deck screen. As such, in at least one example, the whole stillage in line 115 can be separated into the fiber rich portion via line 117 and the filtrate via line 119 with only one or two or more vibratory separators.

The vibratory separator can vibrate, e.g., about its center of mass. The vibration can be induced by eccentric weights on the upper and lower ends of a motion-generator shaft. The vibratory separator can include one or more filter elements, e.g., screen decks, e.g., 1, 2, 3, 4, or more filter elements. The filter element, e.g., screen decks, can have openings of about 10 μm, about 25 μm, about 50 μm, or about 75 μm to about 100 μm, about 130 μm, about 150 μm, about 175 μm, about 230 μm, about 255 μm, about 330 μm, about 380 μm, about 430 μm, about 500 μm, about 700 μm, about 900 μm, about 1 mm, about 1.5 mm, about 2 mm, or more. In some examples, the filter elements can include openings of about 10 μm, about 30 μm, about 50 μm, about 75 μm, about 100 μm, about 125 μm, or about 150 μm to less than 250 μm, less than 300 μm, less than 350 μm, less than 400 μm, less than 450 μm, or less than 500 μm. Some commercially available vibratory separators can include, but are not limited to, the VIBRO-ENERGY® Round Separators, the MX Separators, and the Super MX Separators, available from SWECO, Inc.

In other examples, the separator 116 can be or include one or more centrifugal screeners. In some examples, the separator 116 can be or include a single centrifugal screener. In other examples, the separator 116 can be or include a single centrifugal screener or two or more centrifugal screeners. In other examples, the separator 116 can be or include a single centrifugal screener or two or more centrifugal screeners and can be free of or otherwise exclude any pressure screen, centrifuge, paddle screen, fiber filter, rotary drum screen, brush strainer, rotary vacuum drum filter, vibratory separator, linear motion screen, and vacuum deck screen. As such, in at least one example, the whole stillage in line 115 can be separated into the fiber rich portion via line 117 and the filtrate via line 119 with only one or two or more centrifugal screeners.

The whole stillage can be introduced to an inlet and redirected into a cylindrical sifting chamber via a feed screw. Helical paddles can be rotated within the chamber to propel the whole stillage against a screen, while the resultant, centrifugal force on the particles can accelerate the particles through apertures in the screen. The rotating paddles, which do not contact the screen, can breakup soft agglomerates. Over-sized particles and trash can be ejected via an oversize discharge spout. The screen can have openings of about 10 μm, about 25 μm, about 50 μm, or about 75 μm to about 100 μm, about 130 μm, about 150 μm, about 175 μm, about 230 μm, about 255 μm, about 330 μm, about 380 μm, about 430 μm, about 500 μm, about 700 μm, about 900 μm, about 1 mm, about 1.5 mm, about 2 mm, or more. In some examples, the screen can include openings of about 10 μm, about 30 μm, about 50 μm, about 75 μm, about 100 μm, about 125 μm, or about 150 μm to less than 250 μm, less than 300 μm, less than 350 μm, less than 400 μm, less than 450 μm, or less than 500 μm. A commercially available centrifugal screener can include, but is not limited to, the CENTRI-SIFTER™, available from Kason Corporation.

In other examples, the separator 116 can be or include one or more linear motion screens. In some examples, the separator 116 can be or include a single linear motion screen. In other examples, the separator 116 can be or include a single linear motion screen or two or more linear motion screens. In other examples, the separator 116 can be or include a single linear motion screen or two or more linear motion screens and can be free of or otherwise exclude any pressure screen, centrifuge, paddle screen, fiber filter, rotary drum screen, brush strainer, rotary vacuum drum filter, vibratory separator, centrifugal screener, and vacuum deck screen. As such, in at least one example, the whole stillage in line 115 can be separated into the fiber rich portion via line 117 and the filtrate via line 119 with only one or two or more linear motion screens.

The whole stillage can be introduced to the linear motion screener, which can include an angled filter element, e.g., screen. The filter element can be at an angle of about +10° to about −15° relative to horizontal. The filter element or screen can have openings of about 10 μm, about 25 μm, about 50 μm, or about 75 μm to about 100 μm, about 130 μm, about 150 μm, about 175 μm, about 230 μm, about 255 μm, about 330 μm, about 380 μm, about 430 μm, about 500 μm, about 700 μm, about 900 μm, about 1 mm, about 1.5 mm, about 2 mm, or more. In some examples, the filter element or screen can include openings of about 10 μm, about 30 μm, about 50 μm, about 75 μm, about 100 μm, about 125 μm, or about 150 μm to less than 250 μm, less than 300 μm, less than 350 μm, less than 400 μm, less than 450 μm, or less than 500 μm. A commercially available linear motion screener can include, but is not limited to, the linear motion screeners available from Tinsley Company.

In other examples, the separator 116 can be or include one or more vacu-deck screens. In some examples, the separator 116 can be or include a single vacu-deck screen. In other examples, the separator 116 can be or include a single vacu-deck screen or two or more vacu-deck screens. In other examples, the separator 116 can be or include a single vacu-deck screen or two or more vacu-deck screens and can be free of or otherwise exclude any pressure screen, centrifuge, paddle screen, fiber filter, rotary drum screen, brush strainer, rotary vacuum drum filter, vibratory separator, centrifugal screener, and linear motion screener. As such, in at least one example, the whole stillage in line 115 can be separated into the fiber rich portion via line 117 and the filtrate via line 119 with only one or two or more vacu-deck screens.

The vacu-deck screen can include one or more filter elements or screens that can have openings of about 10 μm, about 25 μm, about 50 μm, or about 75 μm to about 100 μm, about 130 μm, about 150 μm, about 175 μm, about 230 μm, about 255 μm, about 330 μm, about 380 μm, about 430 μm, about 500 μm, about 700 μm, about 900 μm, about 1 mm, about 1.5 mm, about 2 mm, or more. In some examples, the filter element or screen can include openings of about 10 μm, about 30 μm, about 50 μm, about 75 μm, about 100 μm, about 125 μm, or about 150 μm to less than 250 μm, less than 300 μm, less than 350 μm, less than 400 μm, less than 450 μm, or less than 500 μm. A commercially available vacu-deck screen can include, but is not limited to, the vacu-deck screens available from Tinsley Company.

The separator 116, e.g., a pressure screen and/or a fiber filter, can process or filter the whole stillage at a rate of about 94.6 liters per minute, about 379 liters per minute, about 946 liters per minute, or about 1,890 liters per minute to about 2,840 liters per minute, about 3,790 liters per minute, about 4,730 liters per minute, about 5,680 liters per minute, about 6,620 liters per minute, about 7,570 liters per minute, about 11,000 liters per minute, about 15,000 liters per minute, about 19,000 liters per minute, about 22,500 liters per minute, about 26,500 liters per minute, or about 30,500 liters per minute. In one example, the separator, e.g., a pressure screen and/or a fiber filter, can process or filter the whole stillage at a rate of at least 1,890 liters per minute, at least 2,460 liters per minute, at least 3,030 liters per minute, at least 3,600 liters per minute, at least 3,970 liters per minute, at least 4,540 liters per minute, at least 4,920 liters per minute, or at least 5,300 liters per minute to about 5,680 liters per minute, about 6,620 liters per minute, about 7,570 liters per minute, about 12,000 liters per minute, about 20,000 liters per minute, about 26,000 liters per minute, or about 30,500 liters per minute.

In some examples, if the separator 116 is or includes one or more fiber filters, the filtrate via line 119 can contains less solids as compared to if the separator 116 includes one or more centrifuges, one or more pressure screens, one or more paddle screens, or any combination thereof. In other examples, if the separator 116 includes only one or more fiber filters, i.e., does not include a centrifuge, a pressure screen, a paddle screen, or other separator, the filtrate via line 119 can contain less solids as compared to if the separator includes a centrifuge, a pressure screen, a paddle screen, or other separator, but not a fiber filter.

The filtrate can be transferred via line 119 from the separator 116 to one or more centrifuges 120 (e.g., a nozzle centrifuge). The centrifuge 120 can separate or otherwise recover a protein rich portion via line 122 and a clarified stillage via line 121 from the filtrate in line 119. The centrifuge 120 can be provided with washing capabilities so that water, along with the filtrate, can be supplied to the centrifuge 120. The additional water can facilitate separation of the filtrate into the protein rich portion and the clarified stillage. The heavier protein can separate from the lighter components and can be removed as an underflow containing the protein rich portion, whereas the lighter components, which can include oil and starch, can be removed as an overflow containing the clarified stillage. In other examples, the centrifuge 120 can also include or can be replaced with a cyclone separation apparatus or other device to separate the filtrate portion into the protein rich portion and the clarified stillage.

The protein rich portion can be dewatered or otherwise dried such that water can be removed from the protein rich portion to produce a protein rich product. The protein rich portion via line 122 can be transferred from the centrifuge 120 to one or more dryers 124. In some examples, as depicted in FIG. 1, the protein rich portion via line 122 can be transferred to the dryer 124 to reduce the amount of water and/or otherwise dry the protein rich portion to produce a protein rich product. The protein rich product via line 126 can be transferred from the dryer 124 to one or more storage containers 128. In some examples, the separated water portion or filtrate from the dryer 124 can be recycled back or otherwise transferred to the fermenter 108 for liquefaction and/or fermentation. The protein rich product can include less water than the protein rich portion.

The dryer 124 can be or include one or more centrifuges (e.g., a decanter centrifuge), one or more ring dryers (e.g., P-ring dryers), one or more flash dryers, one or more fluid bed dryers, one or more heated air dryers, one or more heaters, one or more steam dryers (e.g., steam ring dryers, steam flash dryers, and/or steam tube dryers), one or more rotary dryers, one or more steam and rotary dryers (e.g., Swiss Combi's ecoDRY™ drying system), one or more superheated steam dryers, one or more spray dryers, one or more vacuum filtration dryers, one or more other drying devices, or any combination thereof to remove water and produce the protein rich product.

The protein rich product in line 126 can be or include high protein corn meal. In some examples, the protein rich product can be used as fish feed, shrimp feed, crab feed, other aquaculture feeds, pig feed, cattle feed, chicken feed, or other livestock feed. The protein rich product can include about 35 wt %, about 40 wt %, or about 45 wt % to about 50 wt %, about 55 wt %, about 60 wt %, about 70 wt %, about 80 wt %, or greater of protein on a dry basis. For example, the protein rich product can include about 35 wt % to about 80 wt %, about 35 wt % to about 70 wt %, about 35 wt % to about 60 wt %, about 35 wt % to about 55 wt %, about 35 wt % to about 50 wt %, about 45 wt % to about 80 wt %, about 45 wt % to about 70 wt %, about 45 wt % to about 60 wt %, about 45 wt % to about 55 wt %, or about 45 wt % to about 50 wt % of protein on a dry basis.

The clarified stillage removed as the overflow in the centrifuge 120 can be transferred via line 121 to one or more evaporators 140. The clarified stillage can be dewatered, i.e., water can be removed from the clarified stillage, to produce an evaporated clarified stillage. For example, the evaporator 140 can gasify at least a portion of the water in the clarified stillage to produce the evaporated clarified stillage.

The evaporated clarified stillage via line 141 can be transferred from the evaporator 140 to one or more oil recovery centrifuges 145 to separate and produce an oil product and an evaporated clarified stillage with reduced oil, also referred to as a stillage with reduced oil. One or more oil products via line 146 can be transferred from the oil recovery centrifuge 145 to one or more storage containers 148. The oil product can include a mixture of typical fatty acids found in corn oil. In some examples, the final recovered oil product can be about 30 wt %, about 40 wt %, about 45 wt % to about 50 wt %, about 60 wt %, or about 70 wt % of the total corn oil in the corn (e.g., corn kernels and/or other corn pieces). The oil recovery centrifuge 145 can function at a higher capacity because the evaporated clarified stillage, which can be subjected to the oil recovery centrifuge 145, can include less water and less protein than the clarified stillage.

The stillage with reduced oil via line 143 from the oil recovery centrifuge 145 can be introduced into one or more evaporators 150. The stillage with reduced oil can be further dewatered or dried in the evaporator 150 where water or other liquids can be further evaporated from the stillage with reduced oil to produce a syrup. The syrup can include, but is not limited to, minerals, sugars, starches, proteins, fibers, other components contained in water, or any mixture thereof. The syrup can be used alone or combined with other components or stream in the separation system 100 to produce various types of products. For example, the syrup via line 151 from the evaporator 150 can be transferred without any further processing to one or more storage containers 152 and can be used or sold as an independent product. In other examples, the syrup via line 153, 157, or 159 can be transferred from the evaporator 150 to one of several portions of the separation system 100 and combined with the fiber rich portion, as will be further discussed and described below.

While the clarified stillage and the stillage with reduced oil can be subjected to the evaporators 140, 150, it should be understood that the number of evaporators and sets thereof can be varied depending on the particular application, conditions, and desired product compositions. In some configurations, each evaporator 140, 150 can be one evaporator or a plurality of evaporators, such as 2, 3, 4, 5, 6, or more evaporators coupled in series and in fluid communication with one another. For example, the evaporator 140 can have three or more evaporators and the evaporator 150 can also have three or more evaporators.

The fiber rich portion via line 117 from the separator 116 can be transferred without any further processing via line 136 to one or more storage containers 138 and referred to as a wet fiber rich product that can be used or sold as an independent product. Alternatively, the fiber rich portion via lines 117 and 154 can be transferred to one or more dryers 160. The fiber rich portion can be further dried or dewatered by the dryer 160 to provide a dried fiber rich product that can be transferred via line 162 to one or more storage containers 164.

The dryer 160 can be or include one or more centrifuges (e.g., a decanter centrifuge), one or more ring dryers (e.g., P-ring dryers), one or more flash dryers, one or more fluid bed dryers, one or more heated air dryers, one or more heaters, one or more steam dryers (e.g., steam ring dryers, steam flash dryers, and/or steam tube dryers), one or more rotary dryers, one or more steam and rotary dryers (e.g., Swiss Combi's ecoDRY drying system), one or more superheated steam dryers, one or more spray dryers, one or more vacuum filtration dryers, one or more other drying devices, or any combination thereof to remove water and produce the protein rich product.

In other examples, the fiber rich portion and the syrup can be combined together. For example, the fiber rich portion via line 117 and the syrup via line 153 from the evaporator 150 can be combined and mixed in line 154 or other processing unit to produce a wet fiber rich product with syrup that can be transferred via line 155 to one or more storage containers 156.

In some examples, the wet fiber rich product with syrup via line 154 can be transferred to the dryer 160. The wet fiber rich product with syrup can be further dried or dewatered by dryer 160 to provide a dried fiber rich product with syrup that can be transferred via line 165 to one or more storage containers 168. The dried fiber rich product with syrup can be used or sold as an independent product.

Alternatively, in other examples, the fiber rich portion and the syrup can be combined together in the dryer 160. For example, the fiber rich portion via lines 117 and 154 and the syrup via line 157 from the evaporator 150 can be combined and mixed in dryer 160 to produce the wet fiber rich product with syrup that can be dried in the dryer 160 to produce the dried fiber rich product with syrup. The dried fiber rich product with syrup can be transferred from the dryer 160 via line 165 to the storage container 168. In other examples, the dried fiber rich product via line 162 from the dryer 160 and the syrup via line 159 from the evaporator 150 can be combined and mixed in line 167 or other processing unit to produce the dried fiber rich product with syrup that can be transferred via line 167 to the storage container 168.

Ground Corn Product

Returning to the ground corn product in line 103, the ground corn product can be quantified by having a particle size distribution, such as by weight percent (wt %) and/or volume percent (vol %), for specified particle sizes. The particle size and the particle size distribution of the ground corn product can be analyzed or otherwise determined by various particle size analyzers, such as laser diffraction analyzers, static and/or dynamic light scattering analyzers, zeta potential analyzers, sieve shaker with graduation test, and others. Generally, the particle size distribution of the ground corn product by weight can be measured using sieves and the particle size distribution of the ground corn product by volume can be measured by laser diffraction, as further discussed and described below.

The particle size and the particle size distribution of the ground corn product by weight can be measured or otherwise determined with a sieve shaker, such as the RO-TAP® RX-29 sieve shaker, commercially available from W. S. Tyler Industrial Group. The sieves analysis can be performed according to the AOAC Official Method 965.22-1966, "Sorting Corn Grits—Sieving Method," available from AOAC International. Sieve sizes of 850 μm, 425 μm, 250 μm, 180 μm, 150 μm, and 105 μm can be used to categorize the particle size distribution of the ground corn product by weight.

The amount of the ground corn product that can have a particle size of 105 μm or less can be about 30 wt %, about 35 wt %, or about 40 wt % to about 45 wt %, about 50 wt %, about 55 wt %, about 60 wt %, about 65 wt %, about 70 wt %, about 75 wt %, or greater, as measured according to AOAC 965.22-1966. For example, about 32 wt % to about 68 wt %, about 41 wt % to about 66 wt %, about 32 wt % to about 62 wt %, or about 35 wt % to about 58 wt % of the ground corn product can have a particle size of 105 μm or less, as measured according to AOAC 965.22-1966. In some examples, greater than 30 wt %, greater than 35 wt %, greater than 40 wt %, greater than 45 wt %, greater than 50 wt %, greater than 55 wt %, greater than 60 wt %, greater than 65 wt %, or greater than 70 wt % of the ground corn product can have a particle size of 105 μm or less, as measured according to AOAC 965.22-1966. In other examples, greater than 25 wt %, greater than 30 wt %, greater than 35 wt %, greater than 40 wt %, greater than 45 wt %, or greater than 50 wt % to about 55 wt %, about 60 wt %, about 65 wt %, or about 70 wt % of the ground corn product can have a particle size of greater than 105 μm, as measured according to AOAC 965.22-1966.

The amount of the ground corn product that can have a particle size of 150 μm or less can be about 41 wt % to about 79 wt %, about 57 wt % to about 90 wt %, about 57 wt % to about 78 wt %, or about 57 wt % to about 75 wt %, as measured according to AOAC 965.22-1966. In some examples, greater than 40 wt %, greater than 50 wt %, greater than 60 wt %, greater than 70 wt %, greater than 75 wt %, or greater than 80 wt % of the ground corn product can have a particle size of 150 µm or less, as measured according to AOAC 965.22-1966.

The amount of the ground corn product that can have a particle size of 180 µm or less can be about 52 wt % to about 97 wt %, about 58 wt % to about 90 wt %, about 56 wt % to about 81 wt %, or about 62 wt % to about 97 wt %, as measured according to AOAC 965.22-1966. In some examples, greater than 50 wt %, greater than 60 wt %, greater than 70 wt %, greater than 80 wt %, greater than 90 wt %, greater than 93 wt %, greater than 95 wt %, or greater than 97 wt % of the ground corn product can have a particle size of 180 µm or less, as measured according to AOAC 965.22-1966.

The amount of the ground corn product that can have a particle size of 250 µm or less can be about 71 wt % to about 98 wt %, about 81 wt % to about 98 wt %, about 91 wt % to about 98 wt %, or about 71 wt % to about 92 wt %, as measured according to AOAC 965.22-1966. In some examples, greater than 70 wt %, greater than 80 wt %, greater than 85 wt %, greater than 90 wt %, greater than 93 wt %, greater than 95 wt %, greater than 96 wt %, greater than 97 wt %, or greater than 98 wt % of the ground corn product can have a particle size of 250 µm or less, as measured according to AOAC 965.22-1966.

The amount of the ground corn product that can have a particle size of 425 µm or less can be about 87 wt % to about 96 wt %, about 87 wt % to about 95 wt %, about 87 wt % to about 99.9 wt %, or about 96 wt % to about 99.9 wt %, as measured according to AOAC 965.22-1966. In some examples, greater than 85 wt %, greater than 86 wt %, greater than 87 wt %, greater than 88 wt %, greater than 89 wt %, greater than 90 wt %, greater than 91 wt %, greater than 92 wt %, greater than 93 wt %, greater than 94 wt %, greater than 95 wt %, greater than 96 wt %, greater than 97 wt %, greater than 98 wt %, greater than 99 wt %, greater than 99.5 wt %, greater than 99.7 wt %, or greater than 99.9 wt % of the ground corn product can have a particle size of 425 µm or less, as measured according to AOAC 965.22-1966. In other examples, greater than 80 wt %, greater than 83 wt %, greater than 85 wt %, greater than 87 wt %, greater than 90 wt %, greater than 93 wt %, or greater than 95 wt % of the ground corn product can have a particle size of 425 µm or less, as measured according to AOAC 965.22-1966. In some examples 100% of the ground corn product can have a particle size of 425 µm or less.

The amount of the ground corn product that can have a particle size of 850 µm or less can be about 98 wt % to about 99.95 wt %, about 99.2 wt % to about 99.9 wt %, about 99.2 wt % to about 99.95 wt %, or about 99.9 wt % to about 99.95 wt %, as measured according to AOAC 965.22-1966. In some examples, greater than 97 wt %, greater than 98 wt %, greater than 99 wt %, greater than 99.3 wt %, greater than 99.5 wt %, greater than 99.7 wt %, greater than 99.9 wt %, greater than 99.91 wt %, greater than 99.93 wt %, or greater than 99.95 wt % of the ground corn product can have a particle size of 850 µm or less, as measured according to AOAC 965.22-1966.

In some examples, about 30 wt % to about 65 wt % of the ground corn product can have a particle size of 105 µm or less; about 40 wt % to about 80 wt % of the ground corn product can have a particle size of 150 µm or less; about 50 wt % to about 97 wt % of the ground corn product can have a particle size of 180 µm or less; about 70 wt % to about 98 wt % of the ground corn product can have a particle size of 250 µm or less; about 85 wt % to about 99.9 wt % of the ground corn product can have a particle size of 425 µm or less; and about 98 wt % to about 99.95 wt % of the ground corn product can have a particle size of 850 µm or less, as measured according to AOAC 965.22-1966. In other examples, greater than 30 wt %, greater than 40 wt %, greater than 50 wt %, or greater than 60 wt % of the ground corn product can have a particle size of 105 µm or less; greater than 40 wt %, greater than 50 wt %, greater than 60 wt %, or greater than 70 wt % of the ground corn product can have a particle size of 150 µm or less; greater than 50 wt %, greater than 60 wt %, greater than 70 wt %, or greater than 80 wt % of the ground corn product can have a particle size of 180 µm or less; greater than 70 wt %, greater than 80 wt %, greater than 90 wt %, or greater than 95 wt % of the ground corn product for a particle size of 250 µm or less; greater than 85 wt %, greater than 90 wt %, greater than 95 wt %, greater than 97 wt %, greater than 99 wt %, greater than 99.5 wt %, or greater than 99.9 wt % of the ground corn product can have a particle size of 425 µm or less; greater than 98 wt %, greater than 99 wt %, greater than 99.5 wt %, greater than 99.9 wt %, greater than 99.93 wt %, or greater than 99.95 wt % of the ground corn product can have a particle size of 850 µm or less, as measured according to AOAC 965.22-1966. In at least one example, greater than 25 wt %, greater than 30 wt %, greater than 35 wt %, greater than 40 wt %, or greater than 45 wt % of the ground corn product can have a particle size of greater than 105 µm, and greater than 80 wt %, greater than 85 wt %, greater than 90 wt %, or greater than 95 wt % of the ground corn product can have a particle size of 425 µm or less, as measured according to AOAC 965.22-1966.

The particle size and the particle size distribution of the ground corn product by volume can be analyzed on a LS™ 13-320 laser diffraction particle size analyzer with a Tornado dry sample module attachment, both commercially available from Beckman Coulter Life Sciences. The laser diffraction particle analysis can be conducted according to the ISO 13320:2009, "Particle Size Analysis—Laser Diffraction Methods," available from International Organization for Standardization.

The amount of the ground corn product that can have a particle size of 25 µm or less can be about 2 vol % to about 10 vol %, about 2 vol % to about 9 vol %, about 2 vol % to about 8 vol %, or about 3 vol % to about 10 vol %, as measured according to ISO 13320:2009. In some examples, greater than 2 vol %, greater than 4 vol %, greater than 6 vol %, greater than 8 vol %, or greater than 9 vol % of the ground corn product can have a particle size of 25 µm or less, as measured according to ISO 13320:2009.

The amount of the ground corn product that can have a particle size of 60 µm or less can be about 16 vol % to about 24 vol %, about 19 vol % to about 25 vol %, about 16 vol % to about 26 vol %, or about 19 vol % to about 28 vol %, as measured according to ISO 13320:2009. In some examples, greater than 10 vol %, greater than 13 vol %, greater than 15 vol %, greater than 17 vol %, greater than 18 vol %, greater than 20 vol %, greater than 22 vol %, greater than 23 vol %, greater than 25 vol %, greater than 28 vol %, greater than t 30 vol %, greater than 35 vol % of the ground corn product can have a particle size of 60 µm or less, as measured according to ISO 13320:2009.

The amount of the ground corn product that can have a particle size of 400 µm or less can be about 42 vol % to about 74 vol %, about 42 vol % to about 71 vol %, about 59 vol % to about 71 vol %, or about 54 vol % to about 71 vol % of the ground corn product can have a particle size of 400 µm or less, as measured according to ISO 13320:2009. In some examples, greater than 40 vol %, greater than 45 vol %, greater than 50 vol %, greater than 55 vol %, greater than 60 vol %, greater than 65 vol %, or greater than 70 vol % of the ground corn product can have a particle size of 400 µm or less, as measured according to ISO 13320:2009.

The amount of the ground corn product that can have a particle size of 800 µm or less can be about 86 vol % to about 90 vol %, about 86 vol % to about 96 vol %, about 87 vol % to about 95 vol %, or about 87 vol % to about 96 vol %, as measured according to ISO 13320:2009. In some examples, greater than 85 vol %, greater than 87 vol %, greater than 89 vol %, greater than 90 vol %, greater than 93 vol %, greater than 94 vol %, or greater than 95 vol % of the ground corn product can have a particle size of 800 µm or less, as measured according to ISO 13320:2009.

In one or more examples, about 10 vol % to about 30 vol % of the ground corn product can have a particle size of 60 µm or less; about 40 vol % to about 70 vol % of the ground corn product can have a particle size of 400 µm or less; and about 85 vol % to about 95 vol % of the ground corn product can have a particle size of 800 µm or less. In other examples, greater than 10 vol %, greater than 15 vol %, greater than 18 vol %, greater than 20 vol %, greater than 25 vol %, greater than 28 vol %, or greater than 30 vol % of the ground corn product can have a particle size of 60 µm or less; greater than 40 vol %, greater than 50 vol %, greater than 55 vol %, greater than 60 vol %, or greater than 70 vol % of the ground corn product can have a particle size of 400 µm or less; and greater than 85 vol %, greater than 90 vol %, or greater than 95 vol % of the ground corn product can have a particle size of 800 µm or less. For example, greater than 18 vol % of the ground corn product can have a particle size of 60 µm or less and greater than 50 vol % of the ground corn product can have a particle size of 400 µm or less, as measured according to ISO 13320:2009.

In some examples, greater than 20 vol % of the ground corn product can have a particle size of 60 µm or less and greater than 60 vol % of the ground corn product can have a particle size of 400 µm or less, as measured according to ISO 13320:2009. In other examples, greater than 18 vol % of the ground corn product can have a particle size of 60 µm or less and greater than 85 vol % of the ground corn product can have a particle size of 800 µm or less, as measured according to ISO 13320:2009. In some examples, greater than 50 vol % of the ground corn product can have a particle size of 400 µm or less and greater than 85 vol % of the ground corn product can have a particle size of 800 µm or less, as measured according to ISO 13320:2009. In other examples, greater than 22 vol % of the ground corn product can have a particle size of 60 µm or less, greater than 60 vol % of the ground corn product having a particle size of 400 µm or less, and greater than 90 vol % of the ground corn product can have a particle size of 800 µm or less, as measured according to ISO 13320:2009.

The volumetric particle size distribution of the ground corn product can be provided by particle size, $d_v$, where v is the volume percent of the ground corn product that has a particle size smaller than the specified value. For example, if the ground corn product has a $d_{10}$ by volume percent of 18 µm, then 10 vol % of the ground corn product has a particle size of less than 18 µm and 90 vol % of the ground corn product has a particle size of 18 µm and larger. In another example, if the ground corn product has a $d_{50}$ by volume percent of 170 µm, then 50 vol % of the ground corn product has a particle size of less than 170 µm and 50 vol % of the ground corn product has a particle size of 170 µm and larger. In another example, if the ground corn product has a $d_{90}$ by volume percent of 800 µm, then 90 vol % of the ground corn product has a particle size of less than 800 µm and 10 vol % of the ground corn product has a particle size of 800 µm and larger.

The ground corn product can have a $d_{10}$ by volume percent of 5 µm, 10 µm, 12 µm, or 15 µm to 20 µm, 25 µm, 30 µm, 40 µm, or 50 µm, as measured according to ISO 13320:2009. For example, the ground corn product can have a $d_{10}$ by volume percent of 10 µm to 30 µm, 10 µm to 25 µm, 10 µm to 20 µm, 12 µm to 30 µm, 12 µm to 25 µm, 12 µm to 20 µm, 14 µm to 30 µm, 14 µm to 25 µm, 14 µm to 20 µm, 15 µm to 25 µm, 16 µm to 30 µm, or 16 µm to 25 µm, as measured according to ISO 13320:2009.

The ground corn product can have a $d_{25}$ by volume percent of 30 µm, 40 µm, or 50 µm to 55 µm, 60 µm, 70 µm, 80 µm, 90 µm, 100 µm, 110 µm, 120 µm, 130 µm, 140 µm, or 150 µm, as measured according to ISO 13320:2009. For example, the ground corn product can have a $d_{25}$ by volume percent of 30 µm to 120 µm, 30 µm to 110 µm, 30 µm to 101 µm, 30 µm to 93 µm, 30 µm to 88 µm, 30 µm to 75 µm, 30 µm to 66 µm, 30 µm to 55 µm, 40 µm to 120 µm, 40 µm to 101 µm, 40 µm to 93 µm, 40 µm to 88 µm, 40 µm to 75 µm, 40 µm to 66 µm, 40 µm to 55 µm, 40 µm to 48 µm, 50 µm to 120 µm, 50 µm to 110 µm, 50 µm to 101 µm, 50 µm to 97 µm, 50 µm to 93 µm, 50 µm to 75 µm, or 50 µm to 66 µm, as measured according to ISO 13320:2009.

The ground corn product can have a $d_{50}$ by volume percent of 100 µm, 110 µm, 125 µm, or 150 µm to 200 µm, 250 µm, 300 µm, 350 µm, 400 µm, 450 µm, or 500 µm, as measured according to ISO 13320:2009. For example, the ground corn product can have a $d_{50}$ by volume percent of 100 µm to 500 µm, 100 µm to 450 µm, 100 µm to 400 µm, 100 µm to 350 µm, 100 µm to 300 µm, 100 µm to 250 µm, 100 µm to 200 µm, 100 µm to 150 µm, 110 µm to 500 µm, 110 µm to 400 µm, 110 µm to 300 µm, 110 µm to 250 µm, 110 µm to 200 µm, 110 µm to 150 µm, 150 µm to 500 µm, 150 µm to 450 µm, 150 µm to 400 µm, 150 µm to 350 µm, 150 µm to 300 µm, 150 µm to 250 µm, 150 µm to 200 µm, or 150 µm to 175 µm, as measured according to ISO 13320:2009.

The ground corn product can have a $d_{75}$ by volume percent of 350 µm, 375 µm, 400 µm, or 425 µm to 450 µm, 500 µm, 550 µm, 600 µm, 650 µm, or 700 µm, as measured according to ISO 13320:2009. For example, the ground corn product can have a $d_{75}$ by volume percent of 350 µm to 700 µm, 350 µm to 650 µm, 350 µm to 600 µm, 350 µm to 550 µm, 350 µm to 500 µm, 350 µm to 450 µm, 350 µm to 400 µm, 375 µm to 700 µm, 375 µm to 600 µm, 375 µm to 500 µm, 375 µm to 450 µm, 375 µm to 400 µm, 400 µm to 700 µm, 400 µm to 600 µm, 400 µm to 500 µm, 425 µm to 700 µm, 425 µm to 650 µm, 425 µm to 600 µm, 425 µm to 550 µm, or 425 µm to 500 µm, as measured according to ISO 13320:2009.

The ground corn product can have a $d_{90}$ by volume percent of 650 µm, 700 µm, 750 µm, or 800 µm to 850 µm, 900 µm, 950 µm, 1,000 µm, 1,050 µm, or 1,100 µm, as measured according to ISO 13320:2009. For example, the ground corn product can have a $d_{90}$ by volume percent of 650 µm to 1,100 µm, 675 µm to 1,100 µm, 700 µm to 1,100 µm, 725 µm to 1,100 µm, 750 µm to 1,100 µm, 800 µm to 1,100 µm, 850 µm to 1,100 µm, 650 µm to 1,000 µm, 675 µm to 1,000 µm, 700 µm to 1,000 µm, 725 µm to 1,000 µm, 750 µm to 1,000 µm, 800 µm to 1,000 µm, 850 µm to 1,000 µm, 650 µm to 950 µm, 700 µm to 950 µm, 725 µm to 950 µm, 750 µm to 950 µm, 800 µm to 950 µm, 850 µm to 950 µm, 650 µm to 900 µm, 675 µm to 900 µm, 700 µm to 900 µm, 750 µm to 900 µm, 800 µm to 900 µm, 650 µm to 850 µm, 675 µm to 850 µm, 700 µm to 850 µm, or 750 µm to 850 µm, as measured according to ISO 13320:2009.

The ground corn product can include, but is not limited to, pericarp particles, floury endosperm particles, germ particles, starch particles, and fiber particles. The starch portions and the germ portions of the corn kernels can be size-reduced to smaller sizes than the fibrous portions of the corn kernels. It is believed that this difference in sizes of the corn portions is a result of the shearing action of the milling device (e.g., air swept pulverizer or disk mill fiberizer). The ground corn product, therefore, can include fiber particles with different particle size distributions than the total particles of the ground corn product.

In one or more examples, the fiber particles of the ground corn product can have a $d_{50}$ by volume percent of 125 µm, 150 µm, or 250 µm to 300 µm, 350 µm, 400 µm, or 500 µm and the total particles of the ground corn product can have a $d_{50}$ by volume percent of 100 µm, 125 µm, or 150 µm to 200 µm, 300 µm, 400 µm, or 500 µm, as measured according to ISO 13320:2009. For example, the fiber particles of the ground corn product can have a $d_{50}$ by volume percent of 125 µm to 450 µm, 150 µm to 450 µm, or 175 µm to 400 µm and the total particles of the ground corn product can have a $d_{50}$ by volume percent of 100 µm to 400 µm, 100 µm to 350 µm, or 125 µm to 300 µm, as measured according to ISO 13320:2009.

In one or more examples, a plurality of total particles of the ground corn product can include a plurality of fiber particles. The fiber particles in the ground corn product can have a $d_{50}$ by volume percent of greater than 160 µm, greater than 180 µm, greater than 200 µm, greater than 250 µm, greater than 300 µm, or greater than 350 µm to 500 µm and the total particles of the ground corn product can have a $d_{50}$ by volume percent of 100 µm to less than 300 µm, less than 350 µm, less than 450 µm, or less than 500 µm, as measured according to ISO 13320:2009. For example, the fiber particles of the ground corn product can have a $d_{50}$ by volume percent of greater than 200 µm and the total particles of the ground corn product can have a $d_{50}$ by volume percent of less than 500 µm, as measured according to ISO 13320: 2009. In another example, the fiber particles of the ground corn product can have a $d_{50}$ by volume percent of greater than 250 µm and the total particles of the ground corn product can have a $d_{50}$ by volume percent of less than 450 µm, as measured according to ISO 13320:2009. In some examples, the fiber particles of the ground corn product can have a $d_{50}$ by volume percent of greater than 300 µm and the total particles of the ground corn product can have a $d_{50}$ by volume percent of less than 400 µm, as measured according to ISO 13320:2009. In other examples, the fiber particles of the ground corn product can have a $d_{50}$ by volume percent of greater than 350 µm and the total particles of the ground corn product can have a $d_{50}$ by volume percent of less than 350 µm, as measured according to ISO 13320:2009. In other examples, the fiber particles of the ground corn product can have a $d_{50}$ by volume percent of greater than 200 µm to 500 µm and the total particles of the ground corn product can have a $d_{50}$ by volume percent of 100 µm to less than 500 µm, as measured according to ISO 13320:2009.

In other examples, the fiber particles of the ground corn product can have a $d_{75}$ by volume percent of 375 µm, 400 µm, or 450 µm to 500 µm, 600 µm, or 700 µm and the total particles of the ground corn product can have a $d_{75}$ by volume percent of 350 µm, 400 µm, or 425 µm to 450 µm, 500 µm, 600 µm, or 700 µm, as measured according to ISO 13320:2009. For example, the fiber particles of the ground corn product can have a $d_{75}$ by volume percent of 375 µm to 700 µm, 400 µm to 600 µm, or 450 µm to 700 µm and the total particles of the ground corn product can have a $d_{75}$ by volume percent of 350 µm to 600 µm, 350 µm to 500 µm, or 325 µm to 550 µm, as measured according to ISO 13320: 2009.

It should be understood that the ground corn product or any portion thereof (e.g., fiber particles) can have a combination of any two or more properties discussed and described above or elsewhere herein. For example, the ground corn product can have a combination of any two, any three, any four, or more, of the following properties: the particle size by weight, the particle size by volume, the particle size distribution by weight, the particle size distribution by volume, the $d_{10}$ value, the $d_{25}$ value, the $d_{50}$ value, the $d_{75}$ value, the $d_{90}$ value, and the crystallinity, which are discussed and described above or elsewhere herein.

The ground corn product and the corn pieces (e.g., corn kernels) from which the ground corn product is ground can have the same composition or substantially the same composition. The corn pieces and the ground corn product can contain, but are not limited to, water, one or more starches (e.g., saccharides and oligosaccharides), one or more proteins, cellulose, one or more oils and/or greases (e.g., saturated and unsaturated fatty acids), one or more volatile organic compounds, other components, or any combination thereof. Generally, for example, the corn pieces and the ground corn product can each include about 5 wt % to about 40 wt % of water, about 15 wt % to about 25 wt % of oligosaccharides, and about 0.5 wt % to about 5 wt % of corn oil.

The corn oil can be or include one or more oils and/or one or more greases which can include one or more saturated fatty acids and/or one or more unsaturated fatty acids. Illustrative saturated fatty acids and unsaturated fatty acids that can be contained in the corn pieces and the ground corn product can be or include caprylic acid, capric acid, myristic acid, palmitic acid, stearic acid, arachidic acid, oleic acid, linoleic acid, linolenic acid, isomers thereof, or any mixture thereof. For example, the corn oil can include about 10 wt % to about 15 wt % of palmitic acid, about 1 wt % to about 2 wt % of stearic acid, about 0.5 wt % to about 2 wt % of arachidic acid, about 20 wt % to about 40 wt % of oleic acid, about 45 wt % to about 65 wt % of linoleic acid, and about 0.5 wt % to about 2 wt % of linolenic acid.

The corn pieces and the ground corn product can include about 0.5 wt %, about 0.8 wt %, about 1 wt %, about 1.5 wt %, or about 1.8 wt % to about 2 wt %, about 2.2 wt %, about 2.5 wt %, about 2.7 wt %, about 3 wt %, about 3.2 wt %, about 3.5 wt %, about 3.7 wt %, about 4 wt %, about 4.5 wt %, or more of corn oil, based on a solids weight of the corn pieces or the ground corn product. For example, the corn pieces and the ground corn product can include about 0.5 wt % to about 4.5 wt %, about 0.5 wt % to about 4 wt %, about 0.5 wt % to about 3.5 wt %, about 0.5 wt % to about 3 wt %, about 0.5 wt % to about 2.5 wt %, about 0.5 wt % to about 2 wt %, about 0.5 wt % to about 1.5 wt %, about 0.5 wt % to about 1 wt %, about 1 wt % to about 4.5 wt %, about 1 wt % to about 4 wt %, about 1 wt % to about 3.5 wt %, about 1 wt % to about 3 wt %, about 1 wt % to about 2.5 wt %, about 1 wt % to about 2 wt %, about 1 wt % to about 1.5 wt %, about 1 wt % to about 1.3 wt %, about 2 wt % to about 4.5 wt %, about 2 wt % to about 4 wt %, about 2 wt % to about 3.5 wt %, about 2 wt % to about 3 wt %, about 2 wt % to about 2.5 wt %, about 2 wt % to about 2.3 wt %, about 2.5 wt % to about 4.5 wt %, about 2.5 wt % to about 4 wt %, about 2.5 wt % to about 3.5 wt %, about 2.5 wt % to about 3 wt %, about 2.5 wt % to about 2.8 wt %, about 3 wt % to about 4.5 wt %, about 3 wt % to about 4 wt %, about 3 wt % to about 3.7 wt %, about 3 wt % to about 3.5 wt %, or about 3 wt % to about 3.2 wt % of corn oil, based on a solids weight of the corn pieces or the ground corn product.

In one or more examples, the corn pieces and the ground corn product can include about 5 wt % to about 40 wt % of water, about 15 wt % to about 25 wt % of soluble starches, about 5 wt % to about 15 wt % of cellulose, and about 0.5 wt % to about 4 wt % of corn oil, based on a solids weight of the corn pieces or the ground corn product. In some examples, the corn pieces and the ground corn product can include about 10 wt % to about 35 wt % of water, about 17 wt % to about 28 wt % of soluble starches, about 10 wt % to about 15 wt % of cellulose, and about 2 wt % to about 4 wt % of corn oil, based on a solids weight of the corn pieces or the ground corn product.

Corn pieces (e.g., corn kernels) can be milled, ground, pulverized, fiberized, or otherwise size-reduced to produce the ground corn product. The corn pieces can also be milled, ground, pulverized, fiberized, or otherwise size-reduced two, three, or more times to produce the ground corn product. The plurality of corn pieces, therefore, can be or include size-reduced corn that is further size-reduced to produce the ground corn product. Illustrative corn pieces that are suitable to be size-reduced can be or include, but are not limited to, whole corn kernels, milled corn kernels, pulverized corn kernels, fiberized corn kernels, ground corn kernels, fragmented corn kernels, crushed corn kernels, smashed corn kernels, shredded corn kernels, other size-reduced corn kernels, fresh corn kernels, dried corn kernels, or any mixture thereof.

In some examples, the corn pieces (e.g., corn kernels) can be size-reduced one or more times with a hammer mill, a roller mill, or other type of mill to produce the plurality of corn pieces that can be further size-reduced one or more times with a high shear mill to produce the ground corn product. For example, the corn pieces can be passed through one or more hammer mills to produce size-reduced corn that subsequently can be passed through a disk mill fiberizer, an air swept pulverizer, and/or any other high shear mills to produce the ground corn product. The ground corn product can be or include fiberized corn, pulverized corn, disk milled corn, other high shear milled corn, or any mixtures thereof.

The corn pieces can be introduced to a high shear mill that can have two rotating surfaces, such as a first rotatable disk and a second rotatable disk. In other examples, the corn pieces can be introduced to a high shear mill that can have one rotating surface and one stationary surface, such as one rotatable disk and one stationary disk, plate, or other surface. The corn pieces can make contact to the two rotating surfaces or can make contact to the one rotating surface and the one stationary surface to mill, shear, grind, fiberize, pulverize, or otherwise size-reduce the corn pieces between the two rotating surfaces or between the one rotating surface and the one stationary surface to produce the ground corn product. For example, the high shear mill can be a disk attrition mill and the corn pieces can be milled or otherwise side-reduced between: a rotatable disk and a stationary disk; a rotatable disk and a stationary surface; or two rotatable disks to produce the ground corn product. In some examples, the corn pieces can be fiberized between two sets of triangular teeth, relatively sharp teeth, or fiberizing teeth of the disk attrition mill to produce fiberized corn product. In other examples, the corn pieces can be pulverized between two sets of rectangular teeth, relatively dull teeth, or pulverizing teeth of the disk attrition mill to produce pulverized corn product. In some examples, at least one disk can have grinding teeth for fiberizing the corn pieces into the ground corn product. Various disk attrition mills can be used to fiberize and/or pulverize. Some disk attrition mills can have a fiberizing side and a pulverizing side which are independent from each other. Disk attrition mills that can be used to mill, grind, or otherwise size-reduce corn can include, for example, the 167.64 cm (66 inch) fiberizer, commercially available from Reynolds Engineering and Equipment, Inc.

In one or more examples, the corn pieces can be introduced into a disk attrition mill, such as a high shear fiberizer or a high shear pulverizer. The disk attrition mill can include a first rotatable disk and either a second rotatable disk or a stationary surface. The disk attrition mill can have at least one set of grinding teeth disposed on each of the first rotatable disk, the second rotatable disk, and the stationary surface. In some configurations, any of the first rotatable disk, the second rotatable disk, or the stationary surface can be free of grinding teeth. In some examples of the disk attrition mill, the first rotatable disk can have a first set of grinding teeth and either the second rotatable disk or the stationary surface is free of grinding teeth. In other examples of the disk attrition mill, the first rotatable disk can have a first set of grinding teeth and either the second rotatable disk or the stationary surface can have a second set of grinding teeth.

The first rotatable disk and either the second rotatable disk or the stationary surface can be separated by a predetermined distance from each other to provide a shearing gap therebetween. The predetermined distance can be fixed or adjustable. If the first rotatable disk and/or either the second rotatable disk or the stationary surface have one or more sets of grinding teeth, then the shearing gap can be measured by the distance between two sets of grinding teeth or between one set of grinding teeth and either the rotatable disk or the stationary surface. For example, the shearing gap can be measured by the distance between the first set of grinding teeth on the first rotatable disk and the second set of grinding teeth on either the second rotatable disk or the stationary surface. In another example, the shearing gap can be measured by the distance between the first set of grinding teeth on the first rotatable disk and either the second rotatable disk or the stationary surface absent of grinding teeth. The shearing gap can be adjusted and/or can be maintained before and/or during the milling of the corn pieces to produce the ground corn product. The shearing gap can be adjusted to produce the ground corn product having the particle size of the ground corn product and a desired distribution of the particle size of the ground corn product. Once the ground corn product is produced within the shearing gap, the ground corn product can pass through the shearing gap to exit the disk mill.

The shearing gap or the distance between the first rotatable disk and/or either the second rotatable disk or the stationary surface can be less than 3,000 µm, less than 2,600 µm, less than 2,000 µm, less than 1,500 µm, less than 1,000 µm, less than 800 µm, less than 500 µm, or less than 250 µm. The shearing gap or the distance between the first rotatable disk and/or either the second rotatable disk or the stationary surface can be about 50 µm, about 100 µm, about 150 µm, or about 250 µm to about 300 µm, about 500 µm, about 700 µm, about 800 µm, about 1,000 µm, about 1,500 µm, about 2,000 µm, about 2,500 µm, or about 2,750 µm. For example, the shearing gap or the distance between the first rotatable disk and/or either the second rotatable disk or the stationary surface can be about 250 μm to about 3,000 μm, about 400 μm to about 2,000 μm, about 500 μm to about 1,000 μm, about 700 μm to about 800 μm, about 700 μm to about 2,800 μm, or about 600 μm to about 2,600 μm.

The corn pieces can be ground, milled, fiberized, pulverized, or otherwise size-reduced to produce the ground corn product that maintains at least a substantial amount of the crystallinity relative to the corn pieces ground to produce the ground corn product. The ground corn product can have a crystallinity that is greater than 75%, about 80%, about 85%, or about 90% to about 92%, about 94%, about 95%, about 96%, about 97%, about 98%, about 99%, about 99.2%, about 99.5%, about 99.7%, about 99.8%, about 99.9%, about 99.95%, about 99.97%, about 99.98%, about 99.99%, or 100%, as compared to the crystallinity of the corn pieces ground to produce the ground corn product. For example, the ground corn product can have a crystallinity that is greater than 75%, greater than 80%, greater than 85%, greater than 90%, greater than 92%, greater than 94%, greater than 95%, greater than 96%, greater than 97%, greater than 98%, greater than 99%, greater than 99.2%, greater than 99.5%, greater than 99.7%, greater than 99.8%, greater than 99.9%, greater than 99.95%, greater than 99.97%, greater than 99.98%, greater than 99.99%, or 100%, as compared to the crystallinity of the corn pieces ground to produce the ground corn product.

For example, the ground corn product can have a crystallinity that is about 80% to 100%, about 85% to 100%, about 90% to 100%, about 95% to 100%, about 97% to 100%, about 98% to 100%, about 99% to 100%, about 99.5% to 100%, about 99.9% to 100%, about 99.95% to 100%, about 75% to about 99%, about 80% to about 99%, about 85% to about 99%, about 90% to about 99%, about 95% to about 99%, about 97% to about 99%, about 98% to about 99%, or about 98.5% to about 99%, as compared to the crystallinity of the corn pieces ground to produce the ground corn product. In other examples, the ground corn product can have a crystallinity that is greater than 75% to 100%, greater than 80% to 100%, greater than 85% to 100%, greater than 90% to 100%, greater than 95% to 100%, greater than 97% to 100%, greater than 98% to 100%, greater than 99% to 100%, greater than 99.5% to 100%, greater than 99.9% to 100%, greater than 99.95% to 100%, greater than 75% to about 99%, greater than 80% to about 99%, greater than 85% to about 99%, greater than 90% to about 99%, greater than 95% to about 99%, greater than 97% to about 99%, greater than 98% to about 99%, or greater than 98.5% to about 99%, as compared to the crystallinity of the corn pieces ground to produce the ground corn product.

The ground corn product can have a crystallinity that is reduced by less than 25%, less than 23%, less than 20%, less than 17%, less than 15%, less than 12%, less than 10%, less than 8%, less than 6%, less than 5%, less than 4%, less than 3%, less than 2%, less than 1%, less than 0.8%, less than 0.5%, less than 0.3%, less than 0.2%, less than 0.1%, less than 0.05%, less than 0.03%, or less than 0.01%, as compared to the crystallinity of the corn pieces ground to produce the ground corn product. For example, the ground corn product can have a crystallinity that is reduced by less than 25% to about 0.001%, less than 25% to about 0.01%, less than 25% to about 0.05%, less than 25% to about 0.1%, less than 10% to about 0.001%, less than 10% to about 0.01%, less than 10% to about 0.05%, less than 10% to about 0.1%, less than 5% to about 0.001%, less than 5% to about 0.01%, less than 5% to about 0.05%, less than 5% to about 0.1%, less than 1% to about 0.001%, less than 1% to about 0.01%, less than 1% to about 0.05%, less than 1% to about 0.1%, less than 0.1% to about 0.001%, less than 0.1% to about 0.01%, less than 0.1% to about 0.08%, or less than 0.1% to about 0.04%, as compared to the crystallinity of the corn pieces ground to produce the ground corn product.

As used herein, the term "crystallinity" refers to a volume ratio of the crystalline portion of cellulose to the total volume of cellulose that includes both the amorphous portion and the crystalline portion. The degree of crystallinity of the ground corn product can be calculated from X-ray diffraction (XRD) data by using a crystalline area integration method based on Cheetham and Leping (Carbohydrate Polymers 36:277-284 (1998)); Nara et al. (Starch 35,12:407-410 (1983)); and Benedetti et al. (Journal of Material Science 18.4:1039-1048 (1983)). The intensities are first normalized over a limited range of data (e.g., 10° to 30° 2-theta). The normalization is determined by a baseline connecting the upper and lower bounds of 10° and 30° 2-theta and then dividing the intensities by the integrated area below the intensities curve and above the baseline. After normalization, a Savitzky-Golay filter is used to smooth the data. The crystalline and amorphous regions can be separated by a function that connects peak baselines. The crystalline portion is the upper region and the amorphous portion is the lower region. The crystalline portion area and the total diffraction area are integrated. The degree of crystallinity is defined as the ratio of the crystalline area over the total diffraction area.

In one or more examples, at least a portion of the corn oil can be extracted or otherwise removed from the ground corn product, the slurry tank mixture containing the ground corn product, the liquefaction mash derived from the ground corn product, the fermentation mash, and/or the stillage. In some examples, the portion of the corn oil that is extracted from the ground corn product is the oil liberated from the corn cellular matrix within the ground corn product and any other oil that is bound by the corn cellular matrix remains in the ground corn product. The corn oil extraction and the corn oil testing can be performed on the SPE-DEX® 3000XL Automated Extractor System and the SPEED-VAP™ Solvent Evaporation System, both commercially available from the Horizon Technology Company, using EPA Method 1664A. The corn oil removed from the ground corn product can be greater than 0.6 wt %, greater than 0.7 wt %, or greater than 0.75 wt % to about 0.9 wt %, about 1 wt %, about 1.2 wt %, or greater of the total weight of the ground corn product. For example, the corn oil removed from the ground corn product can be greater than 0.6 wt % to about 1.2 wt %, greater than 0.65 wt % to about 1.1 wt %, or greater than 0.7 wt % to about 1.05 wt % of the total weight of the ground corn product. In another example, the corn oil removed from the ground corn product, e.g., the stillage, can be greater than 0.6 wt %, greater than 0.7 wt %, greater than 0.75 wt %, greater than 0.8 wt %, or greater than 0.85 wt % to about 0.9 wt %, about 1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 2.3 wt %, about 2.5 wt %, about 2.7 wt %, about 3 wt %, about 3.3 wt %, about 3.5 wt %, about 3.7 wt %, about 4 wt %, or greater of the total weight of the ground corn product.

EXAMPLES

In order to provide a better understanding of the foregoing discussion, the following non-limiting examples are offered.

Although the examples can be directed to specific embodiments, they are not to be viewed as limiting the invention in any specific respect.

Corn Sample Grind Description

For Examples 1-4, the following mill or mills were used as specified in each example. The hammer mill was a Model MG mill, manufactured by Kelly Duplex Mill and Manufacturing Company in Springfield, Ohio. The pulverizer was a Model 16-H air swept pulverizer manufactured by Schutz-O'Neill Company in Minneapolis, Minn. The disk mill fiberizer was a Model TOQ-18 fiberizer, manufactured by Reynolds Engineering & Equipment, Inc. in Muscatine, Iowa.

Ex. 1 was corn that was passed through the hammer mill and through the air swept pulverizer. Raw whole corn kernels were milled to produce hammermilled corn pieces. The hammer mill was operated at about 90 Hz with a tip speed of about 124 meters per second (about 24,500 fpm) using a number 8 screen (3.175 mm) or ($\frac{8}{64}$", or 0.125") at a feed rate of about 925 kg/hr (about 2,040 lbs/hr). The hammermilled corn pieces were pulverized in the air swept pulverizer to produce the ground corn product. The air swept pulverizer was operated at about 80 Hz with a tip speed of about 157 meters per second (about 30,840 fpm) using three 43.18 cm (about 17-inch) diameter CCD beater plates and a CLP liner at a feed rate of about 599 kg/hr (about 1,320 lbs/hr).

Ex. 2 was the same as Ex. 1, but the speed of the air swept pulverizer was reduced as compared to the air swept pulverizer in Ex. 1. Raw whole corn kernels were milled to produce hammermilled corn pieces. The hammer mill was operated at about 90 Hz with a tip speed of about 124 meters per second (about 24,500 fpm) using a number 8 screen (3.175 mm) or ($\frac{8}{64}$", or 0.125") at a feed rate of about 925 kg/hr (about 2,040 lbs/hr). The hammermilled corn pieces were pulverized in the air swept pulverizer to produce the ground corn product. The air swept pulverizer was operated at about 50 Hz with a tip speed of about 97.9 meters per second (about 19,270 fpm) using three 43.18 cm (about 17-inch) diameter CCD beater plates and a CLP liner at a feed rate of about 599 kg/hr (about 1,320 lbs/hr).

Ex. 3 was whole corn that was only run through a disk mill fiberizer. Raw whole corn kernels were milled in the disk mill fiberizer to produce the ground corn product. The disk mill fiberizer used a 45.72 cm (18-inch) diameter TQ18-016 fine tooth plates set with a gap of about 762 μm (about 0.030 inches) and was operated at about 60 Hz with a tip speed of about 124 meters per second (about 24,500 fpm) at a feed rate of about 413 kg/hr (about 910 lbs/hr).

Ex. 4 was corn that was passed through a hammer mill and a disk mill fiberizer. Raw whole corn kernels were milled to produce hammermilled corn pieces. The hammer mill was operated at about 90 Hz with a tip speed of about 124 meters per second (about 24,500 fpm) using a number 8 screen (3.175 mm) or ($\frac{8}{64}$", or 0.125") at a feed rate of about 925 kg/hr (about 2,040 lbs/hr). The hammermilled corn pieces were milled in the disk mill fiberizer to produce the ground corn product. The disk mill fiberizer used 45.72 cm (about 18-inch) diameter TQ18-016 fine tooth plates set with a gap of about 2.54 mm (about 0.100 inches) and was operated at about 60 Hz with a tip speed of about 124 meters per second (about 24,500 fpm) at a feed rate of about 1,890 kg/hr (about 4,170 lbs/hr).

CEx. 1 was corn that was passed through a hammer mill. CEx. 2 was corn that was run through a quad pair set up (a stack of 4 pairs of rolls) roller mill. The corn used in Exs. 1-4 were sourced locally in Muscatine, Iowa; the corn used in CEx. 1 was sourced from a Flint Hills Resources Fairbank facility; and the corn used in CEx. 2 was sourced from RMS in Tea, S. Dak.

Particle Size and Distribution

Table 1 shows the particle size by weight of the ground corn products as measured with sieves for Exs. 1-4 and CExs. 1-2. The sieves analysis was conducted according to the AOAC Official Method 965.22 "Sorting Corn Grits—Sieving Method," available from the AOAC International. The weight percent of the sample that was left on the specified sieve size had a particle size larger than the respective sieve size. For example, in Table 1, the sample particles in Ex. 3 had the following weight percent (wt %) particles for the respective particle sizes: 0.10 wt % larger than 850 μm, 3.60 wt % larger than 425 μm to 850 μm, 4.80 wt % larger than 250 μm to 425 μm, 1.50 wt % larger than 180 μm to 250 μm, 14.90 wt % larger than 150 μm to 180 μm, 9.75 wt % larger than 105 μm to 150 μm, and 65.35 wt % 105 μm or less in the pan.

TABLE 1

Particle Size by Weight (measured with sieves)

| Sieve Size (μm) | Particle Size (μm) | Weight Percent Left on Sieve (wt %) | | | | | |
|---|---|---|---|---|---|---|---|
| | | Ex. 1 | Ex. 2 | Ex. 3 | Ex. 4 | CEx. 1 | CEx. 2 |
| 850 | >850 | 0.05 | 0.05 | 0.10 | 0.60 | 15.00 | 3.01 |
| 425 | >425 to 850 | 0.05 | 5.20 | 3.60 | 12.40 | 25.05 | 27.28 |
| 250 | >250 to 425 | 2.10 | 14.05 | 4.80 | 15.40 | 11.90 | 38.45 |
| 180 | >180 to 250 | 1.20 | 24.55 | 1.50 | 9.10 | 6.30 | 10.40 |
| 150 | >150 to 180 | 21.90 | 15.55 | 14.90 | 4.80 | 3.90 | 9.13 |
| 105 | >105 to 150 | 15.00 | 8.85 | 9.75 | 16.25 | 7.90 | 6.72 |
| pan | 105 and smaller | 59.70 | 31.75 | 65.35 | 41.25 | 29.95 | 5.02 |

Table 2 shows the particle size by volume of the ground corn products and Table 3 shows the particle size distribution by volume of the ground corn products that were analyzed on a LS™ 13-320 laser diffraction particle size analyzer with a Tornado dry sample module attachment, both commercially available from Beckman Coulter Life Sciences. The laser diffraction particle analysis was conducted according to the ISO 13320:2009 "Particle Size Analysis—Laser Diffraction Methods".

The particle size by volume of the ground corn products shown in Table 2 is smaller than the particle size listed. For example: 10 vol % of the particles in the Ex. 3 sample had a particle size smaller than 17.68 μm.

TABLE 2

Particle Size by Volume (measured by laser diffraction)

| vol % | Particle Size (μm) | | | | | |
|---|---|---|---|---|---|---|
| | Ex. 1 | Ex. 2 | Ex. 3 | Ex. 4 | CEx. 1 | CEx. 2 |
| 10 | 18.34 | 24.92 | 17.68 | 21.10 | 88.71 | 135.20 |
| 25 | 54.89 | 101.10 | 47.44 | 92.33 | 282.90 | 304.80 |
| 50 | 168.70 | 287.30 | 167.10 | 285.00 | 686.50 | 531.60 |
| 75 | 404.20 | 630.30 | 486.70 | 587.40 | 1111.00 | 797.10 |
| 90 | 793.30 | 1097.00 | 967.70 | 876.20 | 1450.00 | 1125.00 |

Table 3 gives the complete distribution of particles within each of the listed size ranges. For example: 28.3 vol % of the particles in the Ex. 3 sample had a particle size of greater than 4 μm (e.g., about 4.01 μm) to about 60 μm.

TABLE 3

| | Volume % by Particle Size | | | | | |
|---|---|---|---|---|---|---|
| Particle | Particle Size Distribution (vol %) | | | | | |
| Size (μm) | Ex. 1 | Ex. 2 | Ex. 3 | Ex. 4 | CEx. 1 | CEx. 2 |
| 0-4 | 0 | 0 | 0 | 0 | 0 | 0 |
| >4-60 | 26.3 | 25.1 | 28.3 | 19.6 | 7.8 | 4.9 |
| >60-400 | 48.5 | 49.5 | 42.5 | 40.2 | 23.9 | 29.8 |
| >400-800 | 15.4 | 20.8 | 15.4 | 27.2 | 25.6 | 40.5 |
| >800-2,000 | 9.9 | 4.6 | 13.9 | 13.0 | 42.7 | 24.8 |

Oil and Grease Analysis

Each liquefaction sample was first centrifuged to separate the slurry into separate phases. Each phase was subjected to oil and grease analysis. Oil and grease testing was performed on the SPE-DEX® 3000XL Automated Extractor System and the SPEED-VAP™ Solvent Evaporation System, both commercially available from the Horizon Technology Company. The Horizon Technology automated extraction method, EPA Method 1664A, has been modified and validated to only remove liberated oil from the sample, leaving any oil that may be bound by the corn cellular matrix. The total average weight percent values are listed as the average of two analysis, summarized in Table 4.

TABLE 4

Percent recoveries of each slurry sample level after separation by centrifuge and their averages

| Sample | Total average oil/grease (wt %) |
|---|---|
| Ex. 1 | 0.97 |
| Ex. 2 | 1.01 |
| Ex. 3 | 1.03 |
| Ex. 4 | 0.70 |
| CEx. 1 | 0.26 |
| CEx. 2 | 0.55 |

As shown in Table 4, the average amount of oil/grease recovered in Examples 1-4 was significantly greater than the amount of oil/grease recovered in the Comparative Examples 1 and 2.

Microscopy Analysis

On each selected dry ground sample, microscopy was performed using polarized light and iodine staining on both a Wild Heerbrugg Observation microscope (10×) and an AmScope trinocular microscope (50×-500×). Observation for starch and fiber were noted.

Analytical Methodology

Liquefaction

About 70 g of each ground corn sample was combined with about 200 mL of water having a temperature of about 80° C. to provide a slurry of about 35 wt % of ground corn. About 1 mL of alpha amylase was added to the slurry. Enough 1.2 M HCl was added to each slurry to adjust the pH of the slurry to about 4. Each slurry sample was then placed in a shaker water bath at about 85° C. for about 60 min. After removing slurry sample from the shaker bath, about 0.3 mL of 12 M HCl was added to lower the slurry pH and arrest the amylase activity. The time needed to complete each process of liquefaction for each sample slurry was kept constant to limit sample to sample variability.

Oil and Grease Analysis

About 2 g of each ground corn sample and about 100 mL of diluted distilled water were combined in a vial. Drops of HCl was added to the diluted sample in the vial until the pH of sample was adjusted to less than 2. Oil and grease extraction and testing was performed on the SPE-DEX® 3000XL Automated Extractor System and the SPEED-VAP™ Solvent Evaporation System, both commercially available from the Horizon Technology Company. The sample was processed by the extractor and evaporation systems using hexane as the extraction solvent. The results for the oil and grease analysis are reported in Table 4.

Microscopy Analysis

For Comparative Examples 1-2 and Examples 1-4, microscopy was performed using polarized light and iodine staining on both a Wild Heerbrugg observation microscope having a magnification of 10× (FIGS. 1, 3, 5, 7, 9, and 11) and an AmScope trinocular microscope that had a magnification of 50×-500× (FIGS. 2, 4, 6, 8, 10, and 12).

Iodine Staining Procedure

About 1 g of each ground corn sample was combined with 14 mL distilled water in a 250 mL beaker. About 1 mL of pH 5 buffer was added to the solution. About 84 mL of distilled water was combined with about 1.2 mL of a 0.5 N iodine solution and added to the sample slurry. One or two drops of the sample was transferred to a slide and blended with about 1-2 drops of an aqueous glycerin solution (about 50 wt % of glycerin and about 50 wt % of water). A cover slip was placed on the sample and the sample was observed under the microscope at the referenced magnifications. In the iodine stained sample under polarized light, a distinct Maltese cross formed in each of the starch particles. Particles of fiber and other material appeared brown or showed no color on a lightly blue hued background.

Figures 2, 3:
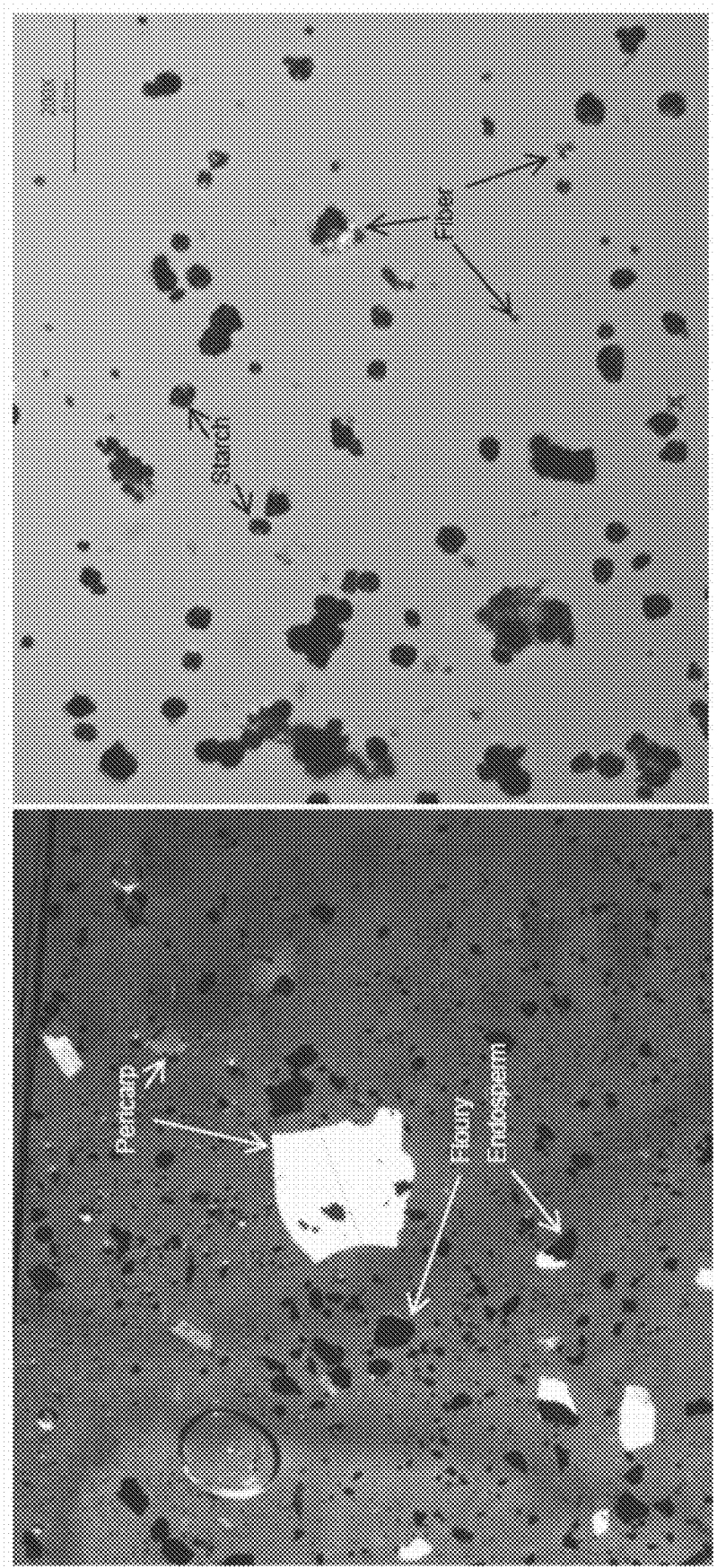
FIG. 2 is an optical microscope image of hammer milled corn (Comparative Example 1) at a magnification of 10×.
FIG. 3 is an optical microscope image of hammer milled corn (Comparative Example 1) at a magnification of 200×.

In the CEx. 1 sample of hammer milled corn, pericarp and floury endosperm particles were viewed at 10× magnification (FIG. 1) and starch and fiber particles were viewed at 200× magnification (FIG. 3).

Figures 4, 5:
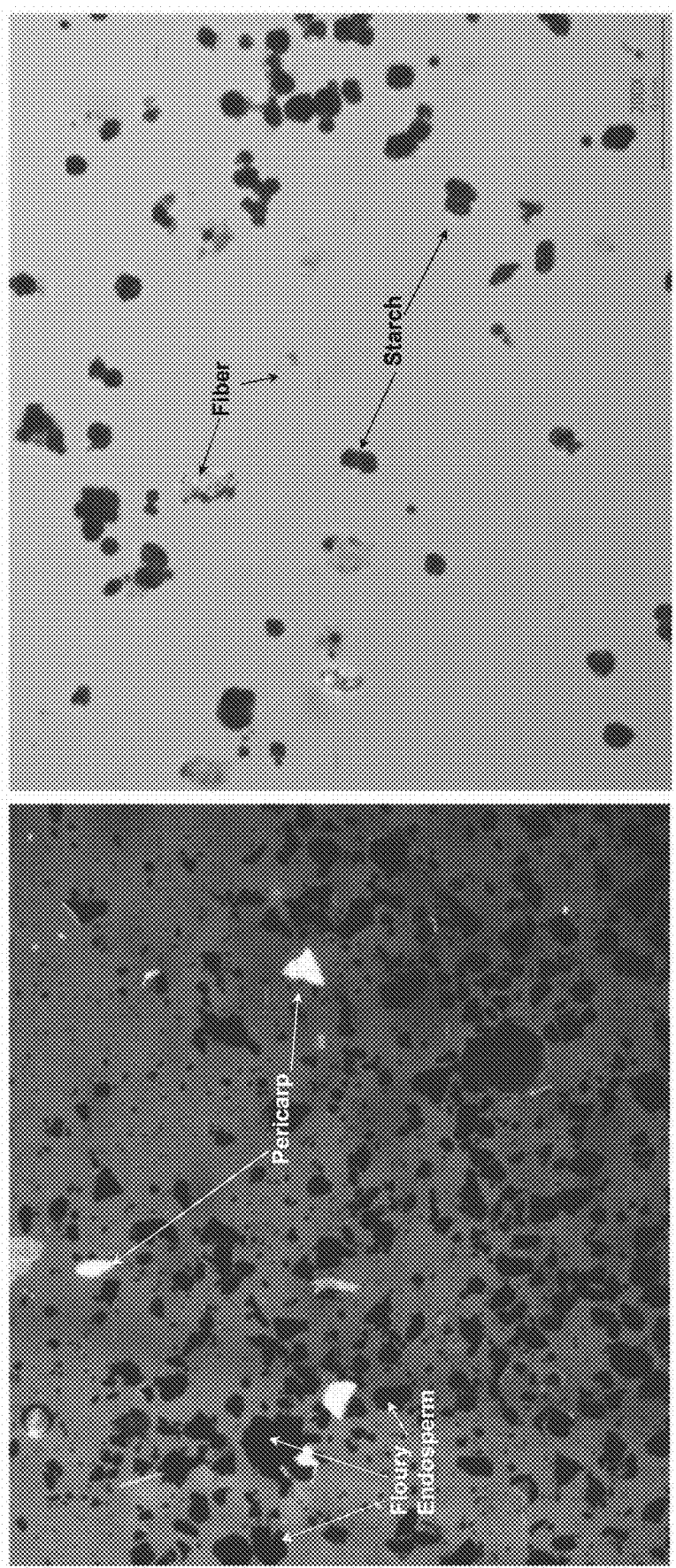
FIG. 4 is an optical microscope image of roller milled corn (Comparative Example 2) at a magnification of 10×.
FIG. 5 is an optical microscope image of roller milled corn (Comparative Example 2) at a magnification of 200×.

In the CEx. 2 sample of roller milled corn, pericarp and floury endosperm particles were viewed at 10× magnification (FIG. 4) and starch and fiber particles were viewed at 200× magnification (FIG. 5).

Figure 7:
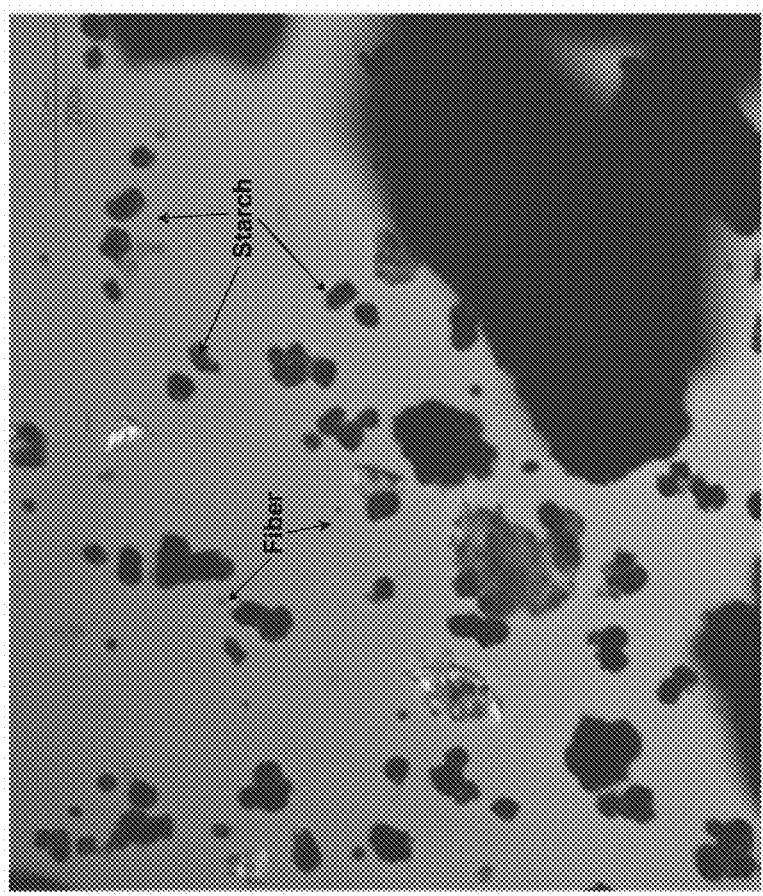
FIG. 7 is an optical microscope image of disk pulverized corn (Example 1) at a magnification of 200×.
Figure 6:
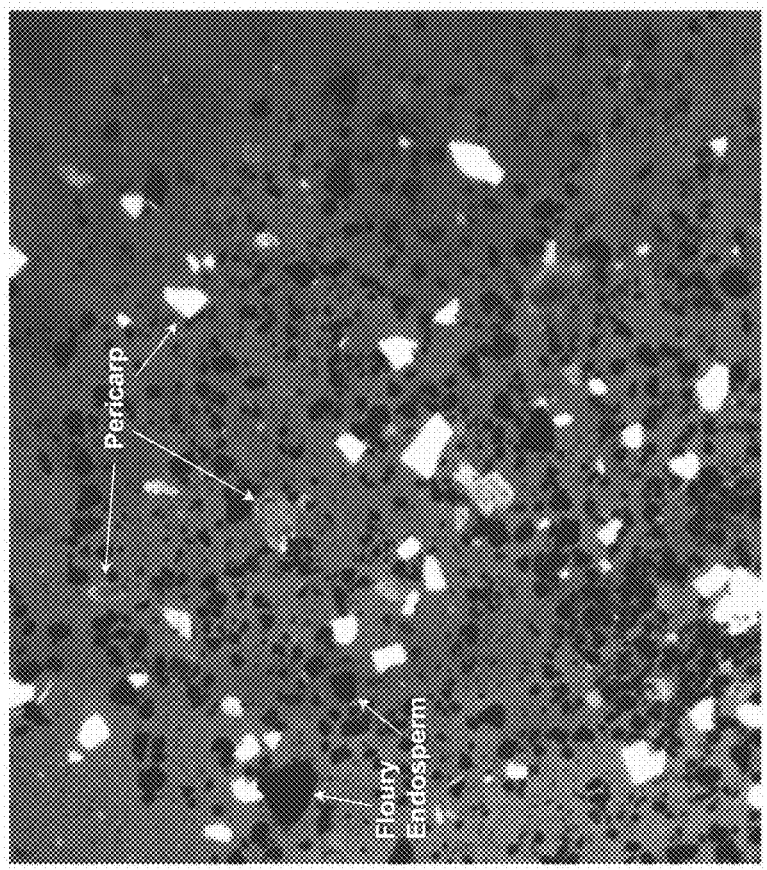
FIG. 6 is an optical microscope image of disk pulverized corn (Example 1) at a magnification of 10×.

In the Ex. 1 sample of disk pulverized corn, pericarp and floury endosperm particles were viewed at 10× magnification (FIG. 6) and starch and fiber particles were viewed at 200× magnification (FIG. 7).

Figure 9:
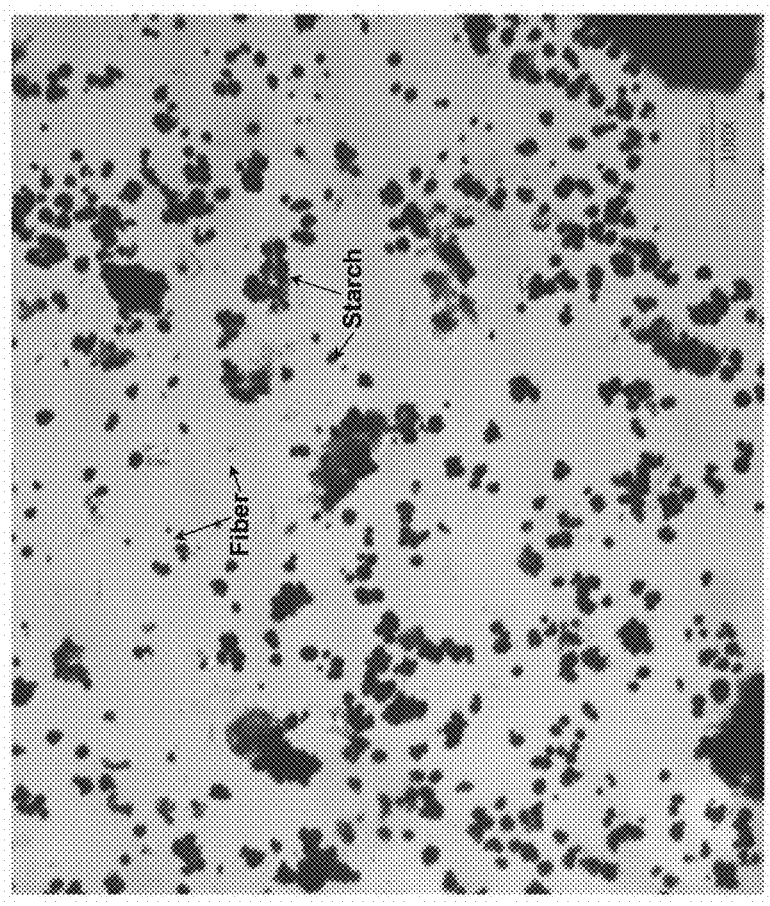
FIG. 9 is an optical microscope image of disk pulverized corn (Example 2) at a magnification of 100×.
Figure 8:
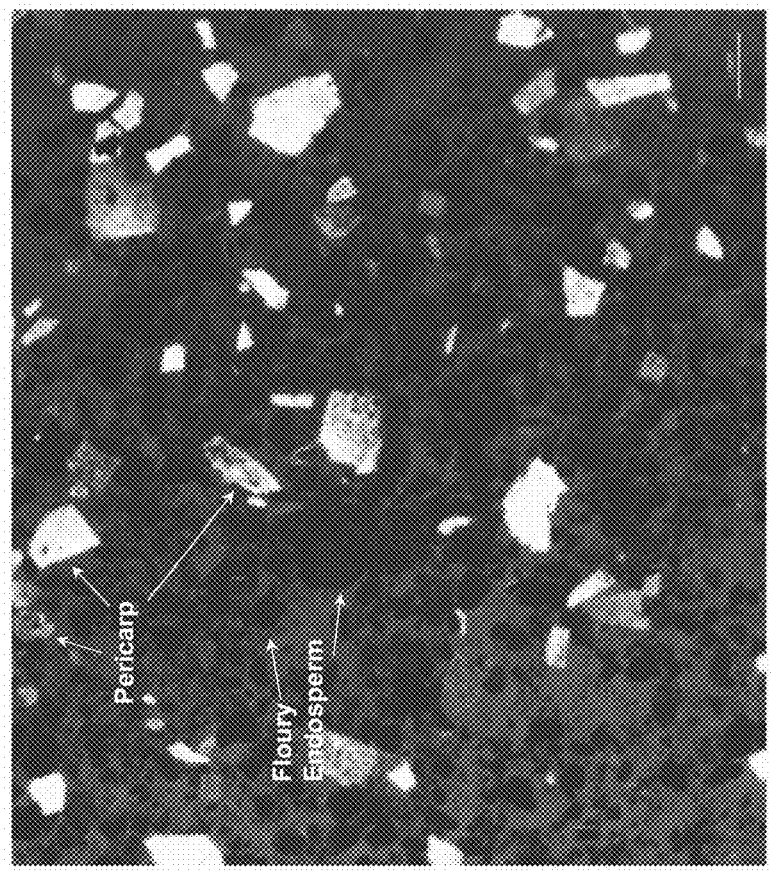
FIG. 8 is an optical microscope image of disk pulverized corn (Example 2) at a magnification of 10×.
Figure 10:
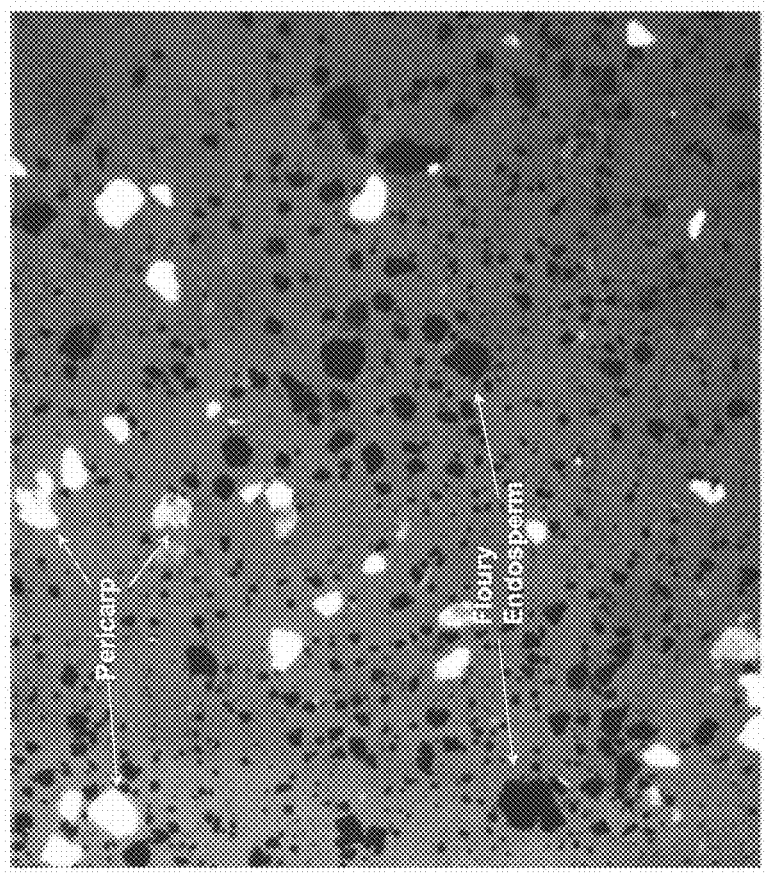
FIG. 10 is an optical microscope image of disk fiberized corn (Example 3) at a magnification of 10×.

In the Ex. 2 sample of disk pulverized corn, pericarp and floury endosperm particles were viewed at 10× magnification (FIG. 8) and starch and fiber particles were viewed at 100× magnification (FIG. 9).

Figure 11:
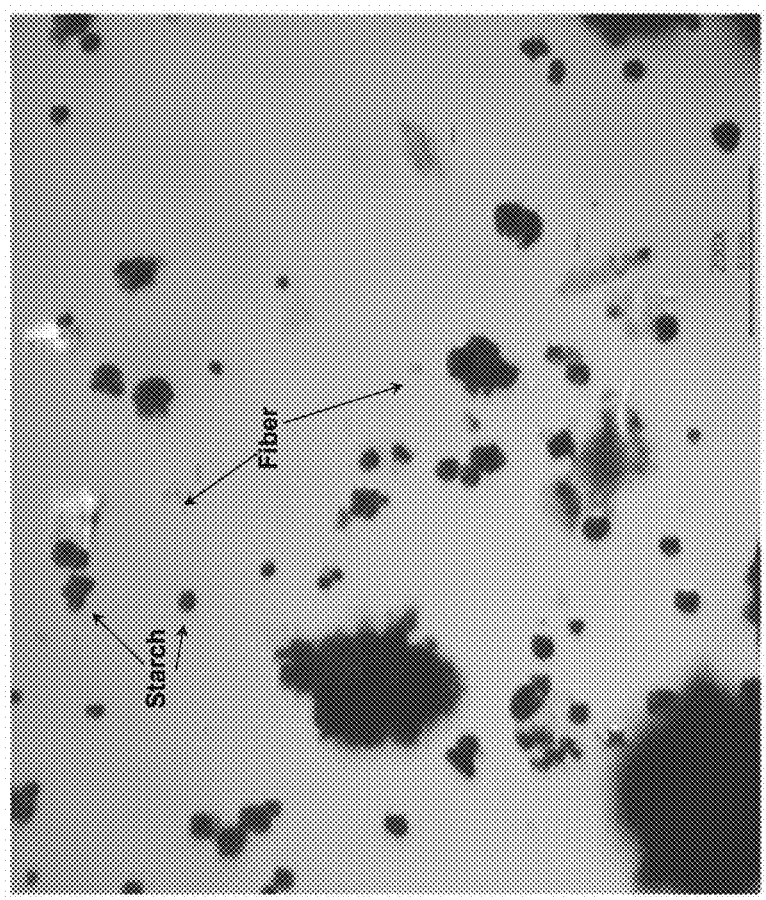
FIG. 11 is an optical microscope image of disk fiberized corn (Example 3) at a magnification of 200×.

In the Ex. 3 sample of disk fiberized corn, pericarp and floury endosperm particles were viewed at 10× magnification (FIG. 10) and starch and fiber particles were viewed at 200× magnification (FIG. 11).

Figures 12, 13:
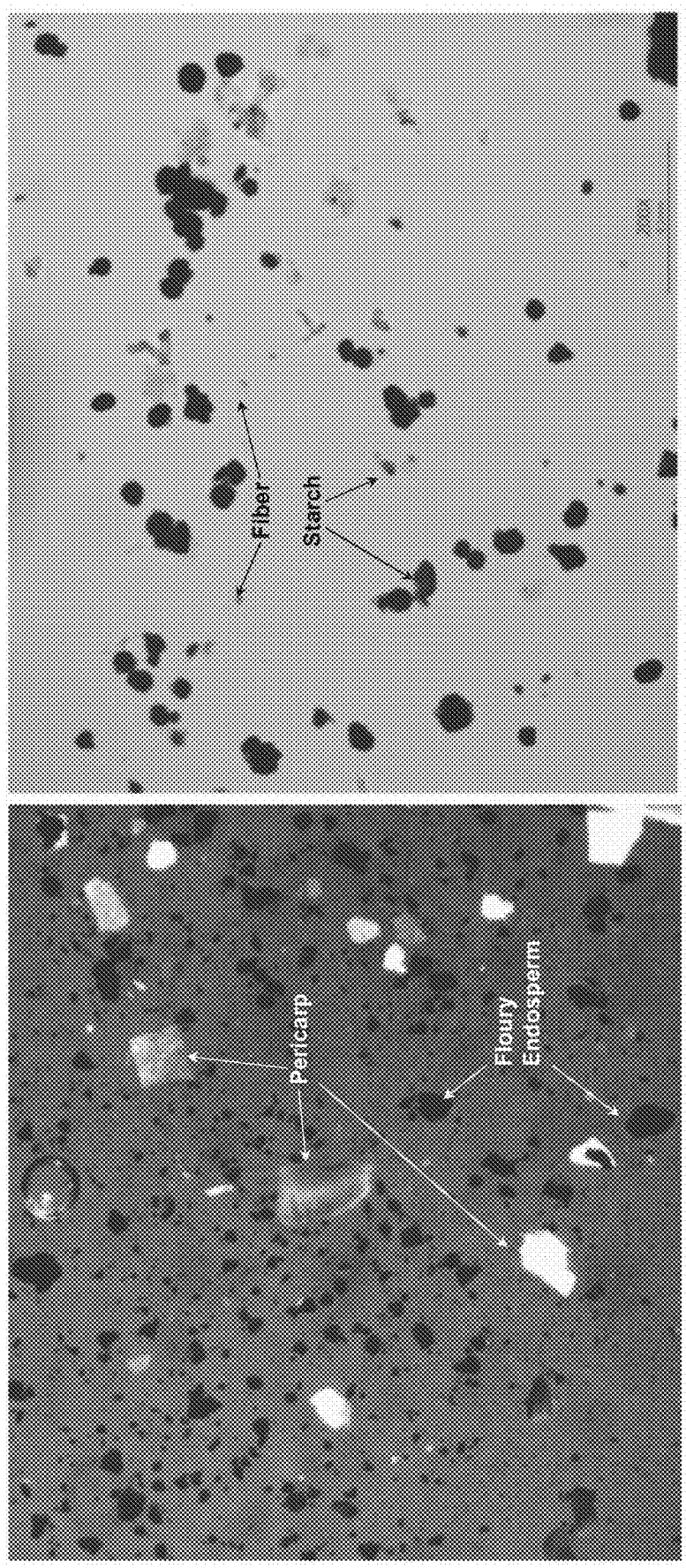
FIG. 12 is an optical microscope image of disk fiberized corn (Example 4) at a magnification of 10×.
FIG. 13 is an optical microscope image of disk fiberized corn (Example 4) at a magnification of 200×.

In the Ex. 4 sample of disk fiberized corn, pericarp and floury endosperm particles were viewed at 10× magnification (FIG. 12) and starch and fiber particles were viewed at 200× magnification (FIG. 13).

Embodiments of the present disclosure further relate to any one or more of the following paragraphs:

1. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, wherein greater than 25 wt % of the ground corn product has a particle size of greater than 105 μm, and wherein greater than 80 wt % of the ground corn product has a particle size of 425 μm or less, as measured according to AOAC 965.22-1966; and separating the whole stillage with a single pressure screen to produce a fiber rich portion and a filtrate.

2. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof; and separating the whole stillage with one or more fiber filters to produce a fiber rich portion and a filtrate.

3. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, wherein greater than 25 wt % of the ground corn product has a particle size of greater than 105 µm, and wherein greater than 80 wt % of the ground corn product has a particle size of 425 µm or less, as measured according to AOAC 965.22-1966; and separating the whole stillage with one or more fiber filters to produce a fiber rich portion and a filtrate.

4. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, wherein greater than 25 wt % of the ground corn product has a particle size of greater than 105 µm, and wherein greater than 80 wt % of the ground corn product has a particle size of 425 µm or less, as measured according to AOAC 965.22-1966; separating the whole stillage to produce a fiber rich portion and a filtrate; separating the filtrate to produce a protein rich portion and a clarified stillage; and removing water from the protein rich portion to produce a protein rich product.

5. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, and wherein the ground corn product has a $d_{50}$ by volume percent of 100 µm to 400 µm, as measured according to ISO 13320:2009; and separating the whole stillage with a single pressure screen to produce a fiber rich portion and a filtrate.

6. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, and wherein the ground corn product has a $d_{50}$ by volume percent of 100 µm to 400 µm, as measured according to ISO 13320:2009; and separating the whole stillage with one or more fiber filters to produce a fiber rich portion and a filtrate.

7. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, and wherein the ground corn product has a $d_{50}$ by volume percent of 100 µm to 400 µm, as measured according to ISO 13320:2009; separating the whole stillage to produce a fiber rich portion and a filtrate; separating the filtrate to produce a protein rich portion and a clarified stillage; and removing water from the protein rich portion to produce a protein rich product.

8. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, and wherein the fiber particles of the ground corn product has a $d_{50}$ by volume percent of greater than 200 µm and the total particles of the ground corn product has a $d_{50}$ by volume percent of less than 500 µm, as measured according to ISO 13320:2009; and separating the whole stillage with a single pressure screen to produce a fiber rich portion and a filtrate.

9. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, and wherein the fiber particles of the ground corn product has a $d_{50}$ by volume percent of greater than 200 µm and the total particles of the ground corn product has a $d_{50}$ by volume percent of less than 500 µm, as measured according to ISO 13320:2009; and separating the whole stillage with one or more fiber filters to produce a fiber rich portion and a filtrate.

10. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, and wherein the fiber particles of the ground corn product has a $d_{50}$ by volume percent of greater than 200 µm and the total particles of the ground corn product has a $d_{50}$ by volume percent of less than 500 µm, as measured according to ISO 13320:2009; separating the whole stillage to produce a fiber rich portion and a filtrate; separating the filtrate to produce a protein rich portion and a clarified stillage; and removing water from the protein rich portion to produce a protein rich product.

11. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, wherein greater than 85 wt % of the ground corn product has a particle size of 425 µm or less, as measured according to AOAC 965.22-1966, and wherein the ground corn product has a crystallinity of greater than 75%, as compared to a crystallinity of the corn pieces; and separating the whole stillage with a single pressure screen to produce a fiber rich portion and a filtrate.

12. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, wherein greater than 85 wt % of the ground corn product has a particle size of 425 µm or less, as measured according to AOAC 965.22-1966, and wherein the ground corn product has a crystallinity of greater than 75%, as compared to a crystallinity of the corn pieces; and separating the whole stillage with one or more fiber filters to produce a fiber rich portion and a filtrate.

13. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, wherein greater than 85 wt % of the ground corn product has a particle size of 425 µm or less, as measured according to AOAC 965.22-1966, and wherein the ground corn product has a crystallinity of greater than 75%, as compared to a crystallinity of the corn pieces; separating the whole stillage to produce a fiber rich portion and a filtrate; separating the filtrate to produce a protein rich portion and a clarified stillage; and removing water from the protein rich portion to produce a protein rich product.

14. The process according to any one of paragraphs 4, 7, 10, and 13, wherein the filtrate is separated by a nozzle centrifuge to produce the protein rich portion and the clarified stillage.

15. The process according to any one of paragraphs 4, 7, 10, and 13, wherein the protein rich portion is dewatered by a decanter centrifuge, a ring dryer, a heated air dryer, a heater, a vacuum filtration dryer, or any combination thereof to produce the protein rich product.

16. The process according to any one of paragraphs 4, 7, 10, and 13, wherein the whole stillage is separated by a pressure screen, a paddle screen, a decanter centrifuge, a filter, or any combination thereof to produce the fiber rich portion and the filtrate.

17. The process according to paragraph 16, wherein the whole stillage is separated by the pressure screen to produce the fiber rich portion and the filtrate.

18. The process according to paragraph 16, wherein the whole stillage is separated by the pressure screen to produce the fiber rich portion and the filtrate, and wherein separation of the whole stillage to produce the fiber rich portion and the filtrate is free of any centrifuge.

19. The process according to paragraph 16, wherein the whole stillage is separated by the filter, and wherein the filter comprises one or more fiber filters.

20. The process according to paragraph 16, wherein the whole stillage is separated by the filter, and wherein the filter comprises one or more fiber filters, and wherein separation of the whole stillage to produce the fiber rich portion and the filtrate is free of any centrifuge.

21. The process according to any one of paragraphs 4, 7, 10, and 13, further comprising: removing water from the clarified stillage to produce an evaporated clarified stillage; and separating the evaporated clarified stillage to produce an oil product and a stillage with reduced oil.

22. The process according to paragraph 21, wherein the evaporated clarified stillage is separated by an evaporator, an oil recovery centrifuge, or both the evaporator and the oil recovery centrifuge to produce the oil product and the stillage with reduced oil.

23. The process according to paragraph 21, further comprising removing water from the stillage with reduced oil to produce a syrup.

24. The process according to paragraph 21, further comprising combining the fiber rich portion and the syrup to produce a wet fiber rich product with syrup or a dried fiber rich product with syrup.

25. The process according to any one of paragraphs 1, 5, 8, and 11, further comprising: separating the filtrate to produce a protein rich portion and a clarified stillage; and removing water from the protein rich portion to produce a protein rich product.

26. The process according to paragraph 25, wherein the filtrate is separated by a nozzle centrifuge to produce the protein rich portion and the clarified stillage.

27. The process according to paragraph 25, wherein the protein rich portion is dewatered by a decanter centrifuge, a ring dryer, a heated air dryer, a heater, a vacuum filtration dryer, or any combination thereof to produce the protein rich product.

28. The process according to paragraph 25, further comprising: removing water from the clarified stillage to produce an evaporated clarified stillage; and separating the evaporated clarified stillage to produce an oil product and a stillage with reduced oil.

29. The process according to paragraph 28, wherein the evaporated clarified stillage is separated by an evaporator, an oil recovery centrifuge, or both the evaporator and the oil recovery centrifuge to produce the oil product and the stillage with reduced oil.

30. The process according to paragraph 28, further comprising removing water from the stillage with reduced oil to produce a syrup.

31. The process according to paragraph 30, further comprising combining the fiber rich portion and the syrup to produce a wet fiber rich product with syrup or a dried fiber rich product with syrup.

32. The process according to any one of paragraphs 1-13, further comprising dewatering the fiber rich portion to produce a dried fiber rich product.

33. The process according to any one of paragraphs 1-13, wherein the ethanol is separated from the fermentation mash by distillation.

34. The process according to any one of paragraphs 1-13, wherein the ground corn product is formed by milling the plurality of corn pieces in an air swept pulverizer or a disk mill fiberizer, and wherein the plurality of corn pieces and the ground corn product have substantially the same composition.

35. The process according to any one of paragraphs 2, 5, 6, 7, 8, 9, 10, 11, and 13, wherein greater than 25 wt % of the ground corn product has a particle size of greater than 105 µm.

36. The process according to any one of paragraphs 2, 5, 6, 7, 8, 9, and 10, wherein greater than 25 wt % of the ground corn product has a particle size of greater than 105 µm, and wherein greater than 80 wt % of the ground corn product has a particle size of 425 µm or less, as measured according to AOAC 965.22-1966.

37. The process according to any one of paragraphs 1-4 and 11-13, wherein the ground corn product has a $d_{50}$ by volume percent of 100 µm to 400 µm, as measured according to ISO 13320:2009.

38. The process according to any one of paragraphs 1-4 and 11-13, wherein the fiber particles of the ground corn product has a $d_{50}$ by volume percent of greater than 200 µm and the total particles of the ground corn product has a $d_{50}$ by volume percent of less than 500 µm, as measured according to ISO 13320:2009.

39. The process according to any one of paragraphs 1-10, wherein greater than 85 wt % of the ground corn product has a particle size of 425 µm or less, as measured according to AOAC 965.22-1966, and wherein the ground corn product has a crystallinity of greater than 75%, as compared to a crystallinity of the corn pieces.

40. The process according to any one of paragraphs 2, 3, 6, 9, and 12, wherein the fiber filter comprises a filter sleeve and a rotor disposed within the filter sleeve.

41. The process according to paragraph 40, wherein the filter sleeve comprises a woven polymer fabric.

42. The process according to any one of paragraphs 2, 3, 6, 9, and 12, wherein the whole stillage is separated at a rate of 25 gallons per minute to about 1,500 gallons per minute with the one or more fiber filters to produce the fiber rich portion and the filtrate.

43. The process according to any one of paragraphs 2, 3, 6, 9, and 12, wherein the filtrate comprises less solids as compared to a comparative filtrate produced by separating the whole stillage with a centrifuge.

44. The process according to any one of paragraphs 2, 3, 6, 9, and 12, wherein the filtrate comprises less solids as compared to a comparative filtrate produced by separating the whole stillage with a pressure screen.

45. The process according to any one of paragraphs 2, 3, 6, 9, and 12, wherein a single fiber filter is used, and wherein the filtrate comprises less solids as compared to a comparative filtrate produced by separating the whole stillage with a single centrifuge.

46. The process according to any one of paragraphs 2, 3, 6, 9, and 12, wherein a single fiber filter is used, and wherein the filtrate comprises less solids as compared to a comparative filtrate produced by separating the whole stillage with a single pressure screen.

47. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, wherein greater than 25 wt % of the ground corn product has a particle size of greater than 105 µm, and wherein greater than 80 wt % of the ground corn product has a particle size of 425 µm or less, as measured according to AOAC 965.22-1966; and separating the whole stillage to produce a fiber rich portion and a filtrate.

48. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof; and separating the whole stillage with one or more fiber filters to produce a fiber rich portion and a filtrate.

49. A process for recovering products from a corn fermentation mash, comprising: separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof; and separating the whole stillage with a separator to produce a fiber rich portion and a filtrate, wherein the separator comprises a rotary drum screen, a rotary vacuum drum filter, a brush strainer, a vibratory separator, a linear motion screen, a vacu-deck screen, or a combination thereof.

50. The process according to any one of paragraphs 47 to 49, further comprising separating the filtrate to produce a protein rich portion and a clarified stillage.

51. The process according to paragraph 50, further comprising removing water from the protein rich portion to produce a protein rich product.

52. The process according to paragraph 50 and 51, further comprising removing water from the clarified stillage to produce an evaporated clarified stillage.

53. The process according to paragraph 52, further comprising separating the evaporated clarified stillage to produce an oil product and a stillage with reduced oil.

54. The process according to any one of paragraphs 47 to 53, wherein the ground corn product has a $d_{50}$ by volume percent of 100 µm to 400 µm, as measured according to ISO 13320:2009.

55. The process according to any one of paragraphs 47 to 54, wherein greater than 85 wt % of the ground corn product has a particle size of 425 µm or less, as measured according to AOAC 965.22-1966

56. The process according to any one of paragraphs 47 to 55, wherein the ground corn product has a crystallinity of greater than 75%, as compared to a crystallinity of the corn pieces.

57. The process according to any one of paragraphs 47 to 56, wherein greater than 90 wt % of the ground corn product has a particle size of 425 µm or less, as measured according to AOAC 965.22-1966.

58. The process according to any one of paragraphs 47 to 57, wherein the ground corn product has a crystallinity of greater than 85%, as compared to a crystallinity of the corn pieces.

59. The process according to any one of paragraphs 47 to 58, wherein the ground corn product has a $d_{50}$ by volume percent of 125 µm to 350 µm, as measured according to ISO 13320:2009.

60. The process according to any one of paragraphs 48 and 50 to 59, wherein the fiber filter comprises a filter sleeve having openings of 500 µm or less.

61. The process according to any one of paragraphs 48 and 50 to 60, wherein the fiber filter comprises a filter sleeve having openings of about 10 µm to less than 400 µm.

62. The process according to any one of paragraphs 48 and 50 to 61, wherein the fiber filter comprises a filter sleeve having openings of about 12 µm to about 200 µm.

63. The process according to any one of paragraphs 48 and 50 to 62, wherein the fiber filter comprises a filter sleeve and a rotor disposed within the filter sleeve, and wherein the filter sleeve comprises a woven polymer fabric.

64. The process according to any one of paragraphs 48 to 63, wherein greater than 25 wt % of the ground corn product has a particle size of greater than 105 µm, and wherein greater than 80 wt % of the ground corn product has a particle size of 425 μm or less, as measured according to AOAC 965.22-1966.

65. The process according to any one of paragraphs 47 to 64, wherein greater than 94 wt % of the ground corn product has a particle size of 425 μm or less, as measured according to AOAC 965.22-1966.

66. The process according to any one of paragraphs 47 to 65 wherein the ground corn product has a $d_{50}$ by volume percent of 120 μm to 350 μm, as measured according to ISO 13320:2009.

67. The process according to any one of paragraphs 49 to 66, wherein the separator comprises the rotary drum screen, the rotary vacuum drum filter, the brush strainer, the vibratory separator, or a combination thereof.

68. The process according to paragraph 67, wherein the separator comprises a filter element having openings of about 10 μm to less than 500 μm.

69. The process according to any one of paragraphs 47 to 49 and 54 to 68, further comprising: separating the filtrate to produce a protein rich portion and a clarified stillage; removing water from the clarified stillage to produce an evaporated clarified stillage; and separating the evaporated clarified stillage to produce an oil product and a stillage with reduced oil.

70. The process according to any one of paragraphs 47, 48, and 50 to 69, wherein the whole stillage is separated in only one fiber filter or two or more fiber filters to produce the fiber rich portion and the filtrate.

71. The process according to any one of paragraphs 47 and 49 to 69, wherein the whole stillage is separated in only one rotary drum screen or two or more rotary drum screens to produce the fiber rich portion and the filtrate.

72. The process according to any one of paragraphs 47 and 49 to 69, wherein the whole stillage is separated in only one rotary vacuum drum filter or two or more rotary vacuum drum filters to produce the fiber rich portion and the filtrate.

73. The process according to any one of paragraphs 47 and 49 to 69, wherein the whole stillage is separated in only one brush strainer or two or more brush strainers to produce the fiber rich portion and the filtrate.

74. The process according to any one of paragraphs 47 and 49 to 69, wherein the whole stillage is separated in only one vibratory separator or two or more vibratory separators to produce the fiber rich portion and the filtrate.

75. The process according to any one of paragraphs 47 and 49 to 69, wherein the whole stillage is separated in only one linear motion screen or two or more linear motion screens to produce the fiber rich portion and the filtrate.

76. The process according to any one of paragraphs 47 and 49 to 69, wherein the whole stillage is separated in only one vacu-deck screen or two or more vacu-deck screens to produce the fiber rich portion and the filtrate.

77. The process according to any one of paragraphs 47 and 49 to 69, wherein the whole stillage is separated in only one pressure screen or two or more pressure screens to produce the fiber rich portion and the filtrate.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. And if applicable, all patents, test procedures, and other documents cited in this application are fully incorporated by reference to the extent such disclosure is not inconsistent with this application and for all jurisdictions in which such incorporation is permitted.

While the foregoing is directed to certain illustrative embodiments, other and further embodiments of the invention can be devised without departing from the basic scope thereof, and the scope thereof is determined by the claims that follow.

What is claimed is:

1. A process for recovering products from a corn fermentation mash, comprising:
    separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, wherein greater than 30 wt % of the ground corn product has a particle size of 105 μm or less, wherein greater than 25 wt % of the ground corn product has a particle size of greater than 105 μm, wherein greater than 80 wt % of the ground corn product has a particle size of 425 μm or less, as measured according to AOAC 965.22-1966, and wherein the ground corn product has a crystallinity that is more than 75% of a crystallinity of the corn pieces; and
    separating the whole stillage with one or more fiber filters to produce a fiber rich portion and a filtrate, wherein the fiber filter comprises a filter sleeve and a rotor disposed within the filter sleeve, wherein the filter sleeve comprises a woven polymer fabric and has openings of about 10 μm to less than 400 μm.

2. The process of claim 1, further comprising:
    separating the filtrate to produce a protein rich portion and a clarified stillage; and
    removing water from the protein rich portion to produce a protein rich product.

3. The process of claim 2, further comprising:
    removing water from the clarified stillage to produce an evaporated clarified stillage; and
    separating the evaporated clarified stillage to produce an oil product and a stillage with reduced oil.

4. The process of claim 1, wherein the ground corn product has a $d_{50}$ by volume percent of 100 μm to 400 μm, as measured according to ISO 13320:2009.

5. The process of claim 1, wherein greater than 85 wt % of the ground corn product has a particle size of 425 μm or less, as measured according to AOAC 965.22-1966.

6. The process of claim 1, wherein greater than 85 wt % of the ground corn product has a particle size of 425 μm or less, as measured according to AOAC 965.22-1966, and wherein the ground corn product has a $d_{50}$ by volume percent of 100 μm to 400 μm, as measured according to ISO 13320:2009.

7. A process for recovering products from a corn fermentation mash, comprising:
    separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, wherein greater than 30 wt % of the ground corn product has a particle size of 105 μm or less, wherein greater than 25 wt % of the ground corn product has a particle size of greater than 105 μm, and wherein greater than 80 wt % of the ground corn product has a particle size of 425 μm or less, as measured according to AOAC 965.22-1966, and wherein the ground corn product has a crystallinity that is more than 75% of a crystallinity of the corn pieces; and separating the whole stillage with one or more fiber filters to produce a fiber rich portion and a filtrate.

8. The process of claim 7, wherein the fiber filter comprises a filter sleeve having openings of 500 μm or less, and wherein the filter sleeve is tensioned with a pair of springs.

9. The process of claim 7, wherein the fiber filter comprises a filter sleeve having openings of about 12 μm to about 200 μm.

10. The process of claim 7, further comprising:
separating the filtrate to produce a protein rich portion and a clarified stillage; and
removing water from the protein rich portion to produce a protein rich product.

11. A process for recovering products from a corn fermentation mash, comprising:
separating ethanol from a fermentation mash to produce a whole stillage, wherein the fermentation mash is derived from a ground corn product milled from a plurality of corn pieces, wherein the plurality of corn pieces comprises whole corn kernels, fragmented corn kernels, size-reduced corn kernels, milled corn kernels, or any mixture thereof, wherein the ground corn product has a crystallinity that is more than 75% of a crystallinity of the corn pieces;
separating the whole stillage with one or more fiber filters to produce a fiber rich portion and a filtrate;
separating the filtrate to produce a protein rich portion and a clarified stillage;
removing water from the clarified stillage to produce an evaporated clarified stillage; and
separating the evaporated clarified stillage to produce an oil product and a stillage with reduced oil.

12. The process of claim 7, wherein the fiber filter comprises a filter sleeve and a rotor disposed within the filter sleeve, and wherein the filter sleeve comprises a woven polymer fabric.

13. The process of claim 11, wherein greater than 30 wt % of the ground corn product has a particle size of 105 μm or less, wherein greater than 30 wt % of the ground corn product has a particle size of greater than 105 μm, and wherein greater than 80 wt % of the ground corn product has a particle size of 425 μm or less, as measured according to AOAC 965.22-1966.

14. The process of claim 7, wherein greater than 94 wt % of the ground corn product has a particle size of 425 μm or less, as measured according to AOAC 965.22-1966, and wherein the ground corn product has a $d_{50}$ by volume percent of 120 μm to 350 μm, as measured according to ISO 13320:2009.

15. The process of claim 7, wherein the whole stillage is separated with the one or more fiber filters in combination with at least one separator to produce the fiber rich portion and a filtrate, the separator selected from the group consisting of: a rotary drum screen, a rotary vacuum drum filter, a brush strainer, a vibratory separator, a linear motion screen, and a vacu-deck screen.

16. The process of claim 7, wherein:
greater than 35 wt % of the ground corn product has a particle size of 105 μm or less and greater than 94 wt % of the ground corn product has a particle size of 425 μm or less, as measured according to AOAC 965.22-1966.

17. The process of claim 1, wherein:
greater than 35 wt % of the ground corn product has a particle size of 105 μm or less and greater than 94 wt % of the ground corn product has a particle size of 425 μm or less, as measured according to AOAC 965.22-1966, and
the ground corn product has a $d_{50}$ by volume percent of 120 μm to 350 μm, as measured according to ISO 13320:2009.

18. The process of claim 7, wherein:
greater than 35 wt % of the ground corn product has a particle size of 105 μm or less and greater than 94 wt % of the ground corn product has a particle size of 425 μm or less, as measured according to AOAC 965.22-1966,
the ground corn product has a $d_{50}$ by volume percent of 120 μm to 350 μm, as measured according to ISO 13320:2009, and
the fiber filter comprises a filter sleeve having openings of about 12 μm to about 200 μm.

19. The process of claim 1, wherein the filter sleeve is tensioned with a pair of springs.

* * * * *